(12) United States Patent
Bolduc et al.

(10) Patent No.: US 6,193,734 B1
(45) Date of Patent: Feb. 27, 2001

(54) SYSTEM FOR PERFORMING VASCULAR ANASTOMOSES

(75) Inventors: Lee R. Bolduc, Mountain View; James R. Gannoe, Redwood City; Philip R. Houle, Palo Alto, all of CA (US)

(73) Assignee: Heartport, Inc., Redwood City, CA (US)

( * ) Notice: Subject to any disclaimer, the term of this patent is extended or adjusted under 35 U.S.C. 154(b) by 0 days.

(21) Appl. No.: 09/227,076

(22) Filed: Jan. 5, 1999

Related U.S. Application Data

(60) Provisional application No. 60/073,294, filed on Jan. 23, 1998.

(51) Int. Cl.[7] .................................................... A61B 17/08
(52) U.S. Cl. ........................... 606/153; 606/213; 606/220
(58) Field of Search ..................... 606/153, 213, 606/216, 220

(56) References Cited

U.S. PATENT DOCUMENTS 5,234,447 * 8/1993 Kaster et al. ......................... 606/153
5,695,504 * 12/1997 Gifford, III et al. ................. 606/153

* cited by examiner

*Primary Examiner*—Michael Buiz
*Assistant Examiner*—Julian W. Woo
(74) *Attorney, Agent, or Firm*—Jens E. Hoekendijk

(57) ABSTRACT

Systems for anastomosing a first hollow tissue structure to a second hollow tissue structure are disclosed. In an exemplary embodiment, such a system comprises at least one tissue securing member adapted to secure the first and second hollow tissue structures together, and a device for applying the tissue securing member to the tissue structures. The tissue securing member is preferably configured to pass through only one of the tissue structures, and is movable from a first configuration to a second configuration which results in a compressive force being applied to the tissue structures. The systems are particularly useful for performing anastomosis of blood vessels in heart surgery.

13 Claims, 20 Drawing Sheets

SYSTEM FOR PERFORMING VASCULAR ANASTOMOSES

CROSS-REFERENCE TO RELATED APPLICATIONS

This application claims priority from co-pending provisional application Ser. No. 60/073,294, filed Jan. 23, 1998.

BACKGROUND OF THE INVENTION

1. Field of the Invention

The invention relates primarily to a system for performing an anastomosis between a first hollow tissue structure, for example, a vascular conduit such as a vein, artery or artificial blood vessel, and a second hollow tissue structure, for example, an aorta or another vascular conduit. The invention may, however, find use in other applications.

2. Description of Related Art

Many devices and methods have been proposed for performing an anastomosis (graft) between blood vessels. One of the most common surgical procedures carried out today which requires performing an anastomosis is coronary artery bypass grafting (CABG), commonly referred to as bypass surgery. This procedure is used to treat patients suffering from coronary disease in the form of one or more coronary arteries that are partially or completely blocked by stenoses. When blood flow through the coronary arteries is restricted or occluded, the cardiac muscle tissue becomes deprived of adequate blood flow, which eventually results in death of the muscle tissue. Interventional procedures other than bypass surgery, for example, angioplasty and atherectomy, are also used to treat occluded coronary arteries. However, bypass surgery is usually desirable or necessary to treat patients suffering from severe or multiple coronary artery blockages, or when other interventional procedures have been or would likely be unsuccessful.

In order to bypass a blockage in a coronary artery, the surgeon must anastomose a vascular conduit which is in communication with a source of arterial blood to the coronary artery at a location downstream of the blockage. The vascular conduit may be a native artery carrying blood from the patient's heart, for example, the right or left internal mammary artery (IMA). In such case, the artery may be transected from the patient's body to provide a free end which is prepared for distal anastomosis to the coronary artery. Alternatively, the IMA may be transected and removed from the body and one end prepared for anastomosis to an arterial blood source and the other to a coronary artery. Further, depending on the number of coronary arteries which are blocked, in addition to using the right and/or left IMA, other vascular conduits may be needed. One end of each conduit is prepared for distal anastomosis to the coronary artery, while the other end is prepared for proximal anastomosis to an arterial blood source, for example, the aorta. The vascular conduits may be harvested from the patient's body, suitable examples of which include the left or right IMA, inferior epigastric artery, splenic artery, subclavian artery, saphenous vein, etc. Also, animal or synthetic vascular conduits may be used instead of or in addition to those mentioned above.

The most common form of bypass surgery involves bypassing blockages in multiple coronary arteries, e.g., quadruple, five or six-way bypass procedures. As a result, most bypass procedures require a number of vascular conduits to form the necessary anastomoses. However, there is a limited number of native arterial conduits available which may be used by simply attaching one end to a blocked coronary artery. As such, it is usually necessary to use free conduits or grafts, which requires forming an anastomosis at both ends of each conduit, one end to an arterial blood source and the other end to the blocked coronary artery. The patient's aorta is a desirable arterial blood source to which the proximal end of one or more conduits may be anastomosed. As is the case with all other anastomoses, the surgeon must securely suture the proximal end of each conduit to the patient's aorta in order to obtain a strong, fluid tight connection, which is a highly technical and time consuming procedure. Nevertheless, when performing bypass surgery via conventional, open-chest procedures in which the patient's sternum is split and retracted, the surgeon has essentially unobstructed access to the heart and aorta, which reduces the difficulty of forming the proximal anastomoses between the vascular conduits and the patient's aorta.

During the last several years, however, there has been a movement away from open-chest surgery toward minimally invasive cardiac surgery. Some of the cardiac procedures presently being performed in a minimally invasive manner include, for example, coronary artery bypass, mitral or aortic valve repair or replacement, and septal defect repair. These procedures are typically carried out through incisions made between the ribs, which requires surgeons to operate with considerably less access to the heart and aorta as compared to open-chest procedures. This reduced access to the heart has increased the difficulty and time associated with forming the anastomoses between the vascular conduits and the patient's arteries, and in particular, the proximal anastomoses between the vascular conduits and the patient's aorta. More specifically, the already highly technical procedure of suturing the vascular conduits to the aorta or other arterial blood source (as well as to the coronary arteries) is even more difficult when the surgeon is operating through a small port, e.g., an incision 3 or 4 inches in length. As a secure, fluid tight anastomosis is highly desirable in order to provide long term patency of the conduit bypassing the blockage, minimally invasive cardiac surgery presents significant challenges for the surgeon.

The devices and methods used in conventional open-chest cardiac surgery, however, are not always usable or readily adaptable to carry out minimally invasive cardiac surgery. The use of suture to form the anastomoses in the standard in cardiac surgery. As noted above, though, using suture to anastomose the respective vascular conduits is particularly difficult when performing a minimally invasive cardiac procedure. Although stapling devices are commonly used during laparoscopic procedures to join various tissue structures, they are not designed or easily adaptable for use in minimally invasive cardiac surgery. As a result, there is a need in the art for an effective alternative to using suture in order to carry out minimally invasive cardiac procedures, and in particular forming anastomoses between hollow tissue structures when access to the tissue is limited.

SUMMARY OF THE INVENTION

According to one aspect of the invention, a system is provided for anastomosing a first hollow tissue structure to a second hollow tissue structure. In one preferred embodiment, the system comprises at least one tissue securing member adapted to secure the first and second hollow body structures together, and a device for applying the member to the tissue structures. The tissue securing member is preferably configured to secure the tissue structures together by passing through only one of the tissue structures.

The member is carried on an applier in a first configuration and is changed into a second, different configuration which results in a compressive force being applied to the tissue structures, thereby securing the tissue structure together in fluid communication.

In a more specific preferred embodiment, the member is in a first configuration and is permanently deformed to assume the second configuration. In another specific preferred embodiment, the member is formed so that it assumes a first configuration when unbiased, is biased into a second configuration when initially engaged with the first tissue structure, and then is permitted to return to the first configuration in order to secure the tissue structures together.

The tissue securing members are preferably separate, discrete elements that are spaced around the anastomosis. Additionally, in one specific preferred embodiment, the members are the only structure that exerts compressive force to join the tissue structures. In another specific preferred embodiment, the members are coupled to a hub that also exerts compressive force on the tissue structures.

In another aspect of the invention, a method of anastomosing a first hollow tissue structure to a second hollow tissue structure is provided. In one preferred embodiment, the method comprises passing a first portion of at least one anastomosis device in a first configuration through an end of a first hollow tissue structure, and positioning the end of the first hollow tissue structure and the first portion of the anastomosis device through an opening formed in a wall of a second hollow tissue structure. The first and second hollow tissue structures are secured together by changing the configuration of the anastomosis device to compress the end of the first hollow tissue structure against the wall of the second hollow tissue structure, this step preferably being performed without passing the anastomosis device through the second hollow tissue structure. As a result, the first hollow tissue structure is secured in communication with the opening in the second hollow tissue. As an example, in one preferred application the first hollow tissue structure is a vascular conduit and the second hollow body structure is a patient's aorta.

In a more specific preferred embodiment, the end of the first hollow tissue structure is everted and the tissue securing element, in a first configuration, is passed through the everted end and then positioned in the opening in the second hollow tissue structure. The configuration of the securing element is then changed to form the anastomosis by securing the first and second hollow tissue structures together.

BRIEF DESCRIPTION OF THE DRAWING FIGURES

Other features, benefits and advantages of the invention will be apparent from the detailed description of preferred embodiments which follows, taken in conjunction with the accompanying drawing Figures, wherein.

Figure 29A:
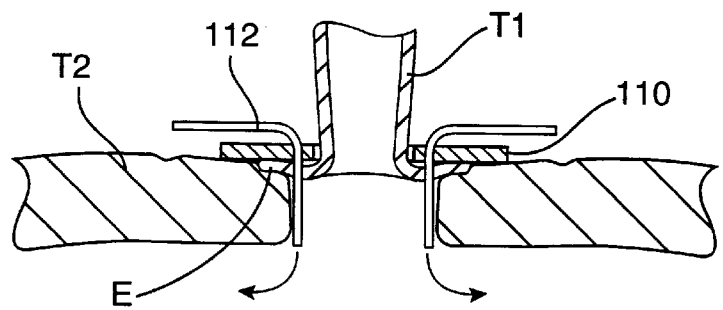
Figure 29B:
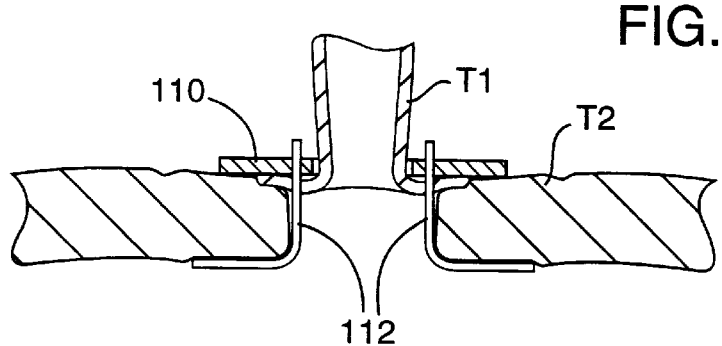
Figure 30A:
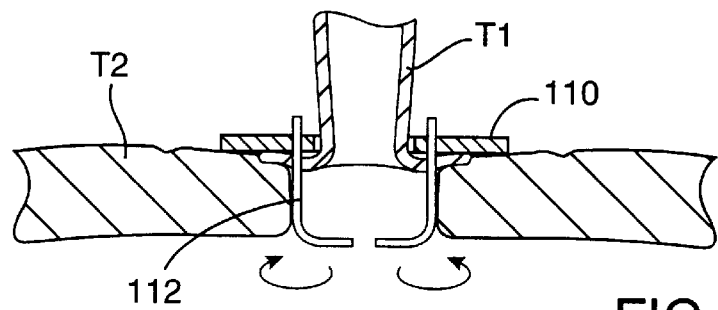
Figure 30B:
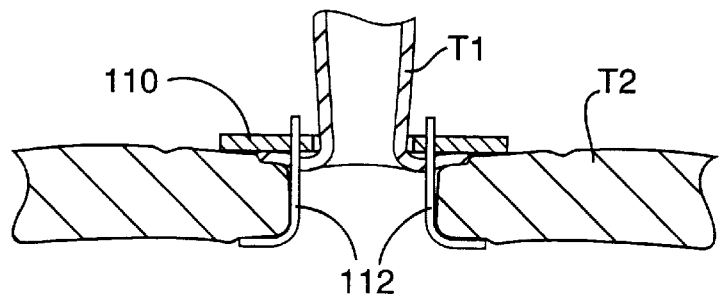

FIGS. 29A and 29B are sectional views of an anastomosis including a hub and tissue securing members constructed according to another embodiment of the invention, showing the sequence in which the members are actuated to compress the first and second hollow tissue structures together; and FIGS. 30A and 30B are sectional views of an anastomosis including a hub and tissue securing members constructed according to still another embodiment of the invention, the Figures showing the sequence in which the members are actuated to compress the first and second hollow tissue structures together.

DETAILED DESCRIPTION OF PREFERRED EMBODIMENTS

The present invention provides an anastomosis system comprising various devices and associated methods of using the devices to perform anastomosis of hollow tissue structures, which may be vascular or nonvascular structures. The devices and methods will be described in connection with a preferred application thereof, namely, coronary artery bypass grafting during which a vascular conduit, such as a vein, artery, or artificial conduit, is anastomosed to an aorta. It will be understood that the invention will find use in various other applications not specifically described herein.

Figure 1:
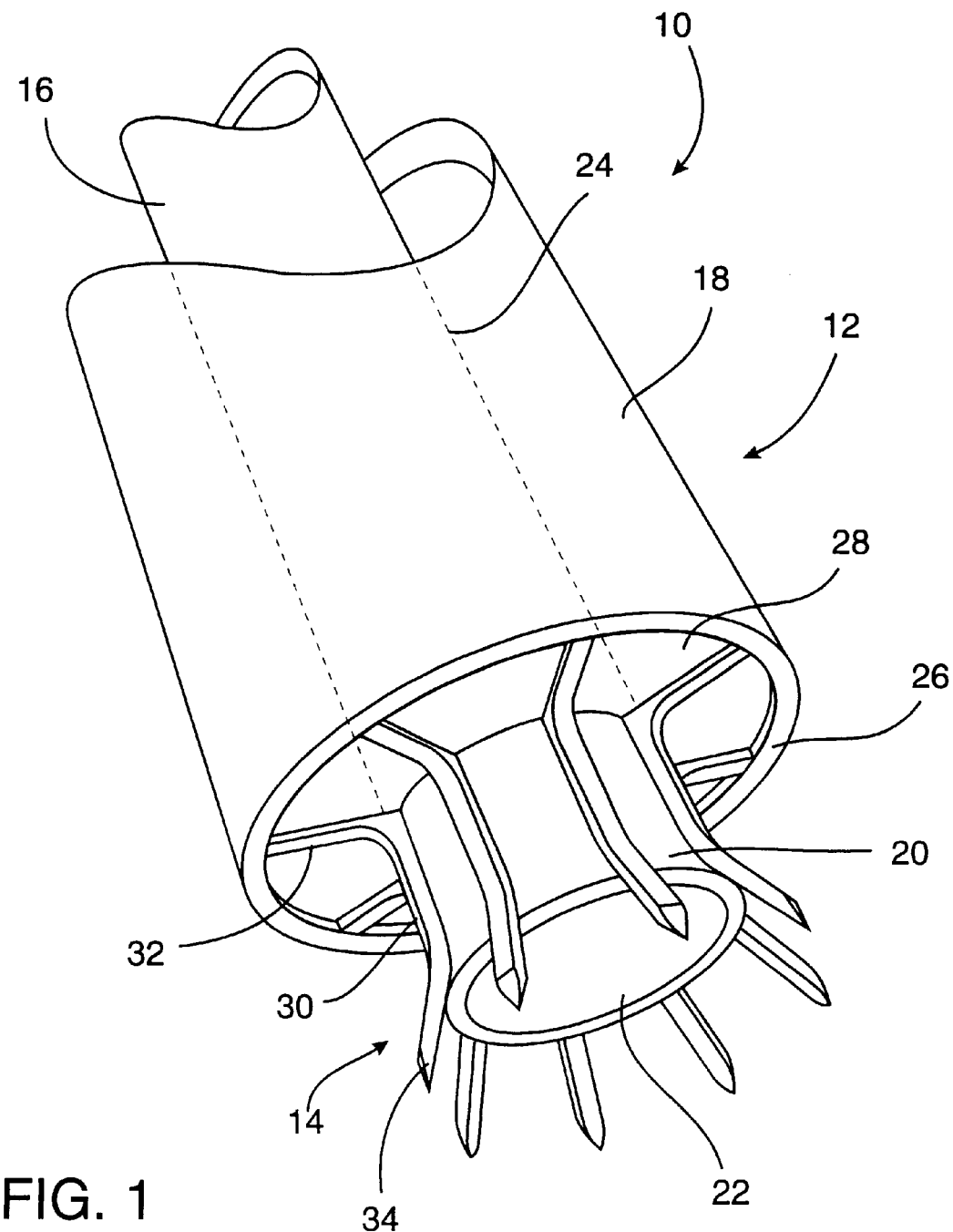
FIG. 1 is a perspective view of an anastomosis system constructed according to one embodiment of the invention, the system comprising an applier loaded with tissue securing members for anastomosing a first hollow tissue structure to a second hollow tissue structure.

With the foregoing as background, FIG. 1 illustrates an anastomosis system indicated generally by the reference numeral 10 which comprises an applier 12 and a plurality of tissue securing members 14. The applier 12 includes first and second applier members 16, 18 which are relatively movable. In the illustrated embodiment, the member 16 is positioned within the member 18 in a sliding, telescoping manner; however, it will be recognized that alternative configurations may be used to achieve relative movement between the first and second applier members.

The preferred applier member 16 is in the form of an elongate body terminating in a bell-shaped end 20 and having a hollow interior defining a bore 22 configured to receive a first hollow tissue structure so that an end of the structure extends beyond the bell-shaped end 20. The preferred applier member 18 also is in the form of a hollow body and defines a bore 24 in which the member 16 is slidably positioned. The member 18 terminates in an end defining a rim or flange 26 which cooperates with an end surface 28 to form a recess configured to receive the tissue securing members 14. In the embodiment shown in FIG. 1, the tissue securing members 14 are formed in a first configuration which is generally L-shaped and comprises a first leg 30 which is shaped to extend along the bell-shaped end 20 of the applier member 16, and a second leg 32 which sits in the recess defined by the end surface 28 and rim 26. The tissue securing members 14 are sized and configured so that they are retained by compressive force exerted by the first and second applier members 16, 18. The first leg 30 of each securing member 14 terminates in a sharpened tip 34 configured to be passed through a first hollow tissue structure (not shown in FIG. 1).

Figure 2:
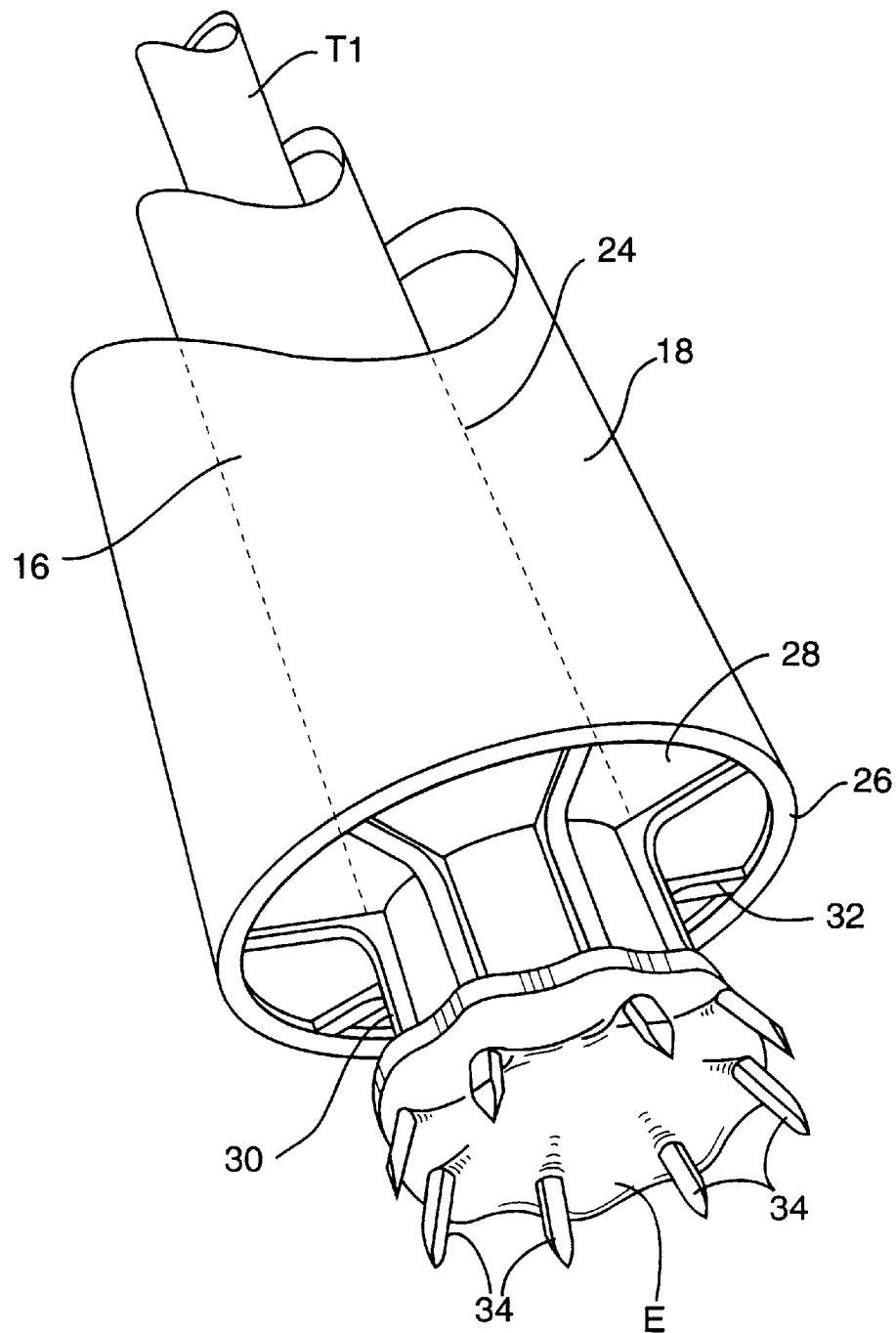
FIG. 2 is a perspective view of the system shown in FIG. 1, after a first hollow tissue structure has been loaded on the applier.

FIG. 2 shows the anastomosis system 10 after a first hollow tissue structure T1 has been loaded onto the applier 12 and engaged with the tissue securing members 14. The tissue structure T1, which in the illustrated embodiment is a vascular conduit such as an artery, vein or artificial conduit, is passed through the bore 22 in the applier member 16 by any suitable means. For example, a snare may be threaded through the bore 22 and engaged with the tissue structure T1 to pull the structure through the bore until the end E of the structure extends slightly beyond the bell-shaped end 20 of the applier member 16. The end E of the tissue structure T1 is then everted as shown and pushed over the sharpened tips 34 of the tissue securing members 14, the resulting configuration being shown in FIG. 2. The tips 34 of the securing members 14 are preferably passed through the everted end E a sufficient distance from the edge of the tissue structure T1 to obtain a firm grip while minimizing the possibility of tearing the tissue. Also, while in the illustrated embodiment the end of the first tissue structure T1 is everted approximately 90°, it will be appreciated that it may be everted more or less than 90°.

Figure 3:
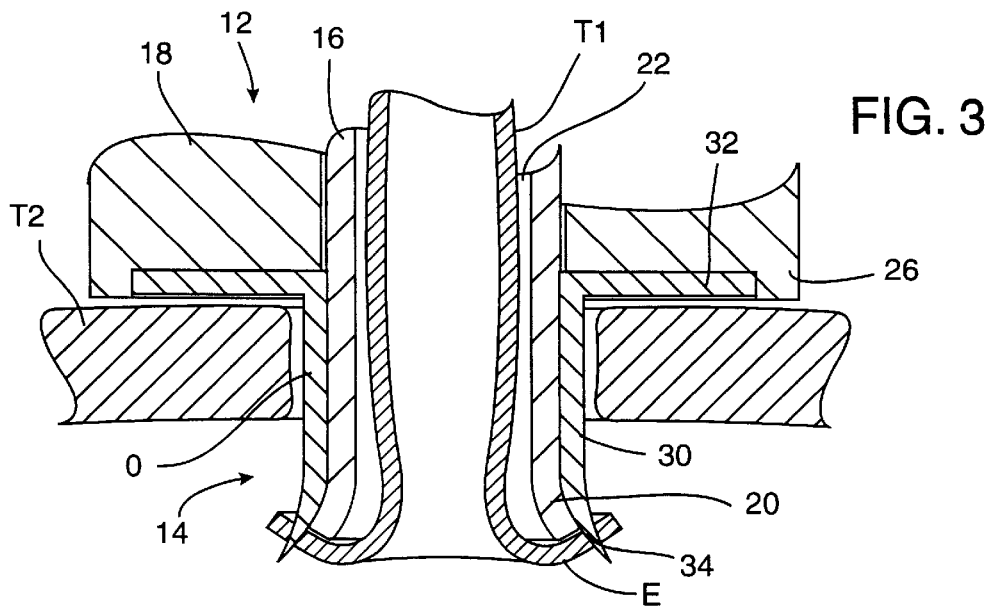
FIG. 3 is a sectional view of the system shown in FIG. 2, after the applier has been positioned in an opening formed in a second hollow tissue structure.
Figure 4:
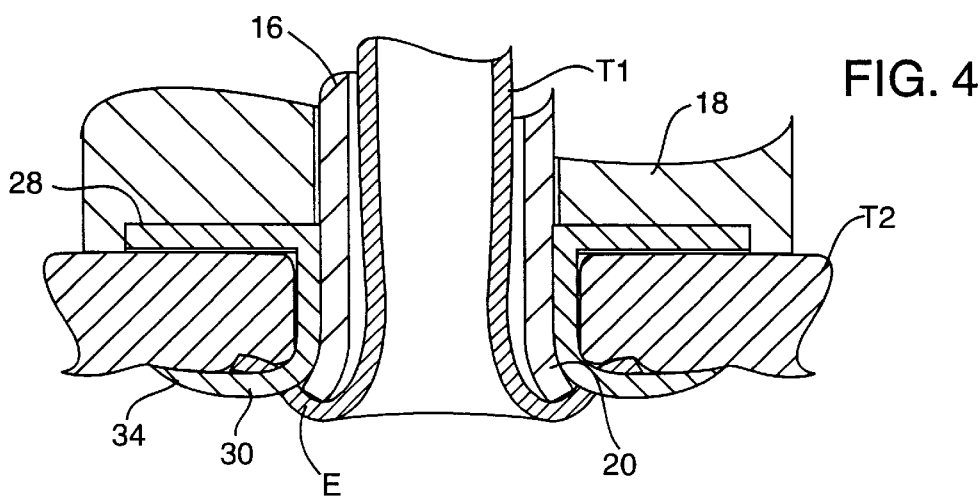
FIG. 4 is a sectional view corresponding to FIG. 3, after the applier has been actuated to apply the tissue securing members and anastomose the first hollow tissue structure to the second hollow tissue structure.
Figure 5:
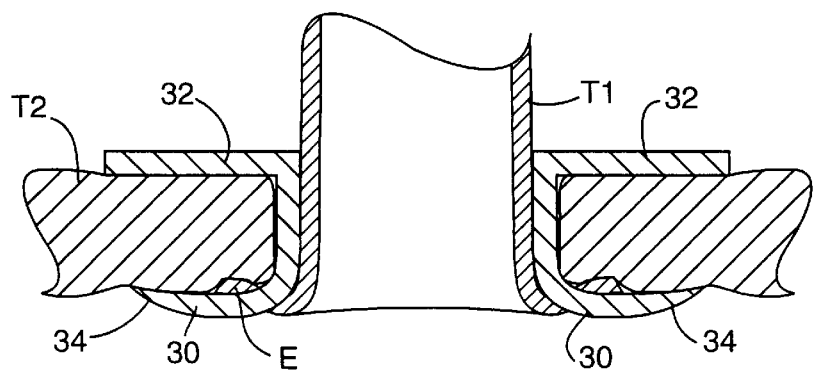
FIG. 5 is a sectional view corresponding to FIG. 4, showing the anastomosis after the applier has been removed from the hollow tissue structures.

Next, referring to FIGS. 3–5, the applier 12, tissue securing members 14, and first hollow tissue structure T1 are positioned against a second hollow tissue structure T2 through which an opening O has been formed. In the illustrated embodiment, the second hollow tissue structure T2 is an aorta and the opening O is an aortotomy formed in the wall of the aorta by suitable means, for example, an aortic punch (not shown). As shown in FIG. 3, the first tissue structure T1 and the securing members 14 are passed through the opening O so as to be in close proximity to the edge of the opening O with the legs 32 of the members 14 pressed against the wall of structure T2. The applier 12 is then actuated to manipulate the tissue securing members 14 from their first configuration to a second, different configuration which results in compressing the everted end E of the first tissue structure T1 against the interior surface of the wall of the second tissue structure T2.

In the illustrated embodiment, the tissue securing members 14 are formed of a rigid material, such as stainless steel or other suitable implantable materials, and actuation of the applier 12 deforms the members 14 from their first configuration (FIG. 3) to a second configuration (FIGS. 4 and 5). This is achieved by moving the applier member 16 away from the second tissue structure T2 with respect to the applier member 18. This causes the bell-shaped end 20 of the applier member 16 to fold the first leg 30 of each tissue securing member 14 toward the second leg 32 and into contact with the wall of the second tissue structure T2, which sandwiches the end E of the first tissue structure T1 between the leg 30 and the tissue structure T2. The members 14 and the applier member 16 are complementarily configured so that when each member 14 has been collapsed to its second configuration the applier member 16 can be slid out of the opening O and removed along with the applier member 18, leaving a secure, leak tight anastomosis as shown in FIG. 5. The applier members 16, 18 are preferably formed of a rigid, sturdy material such as stainless steel.

Figure 6:
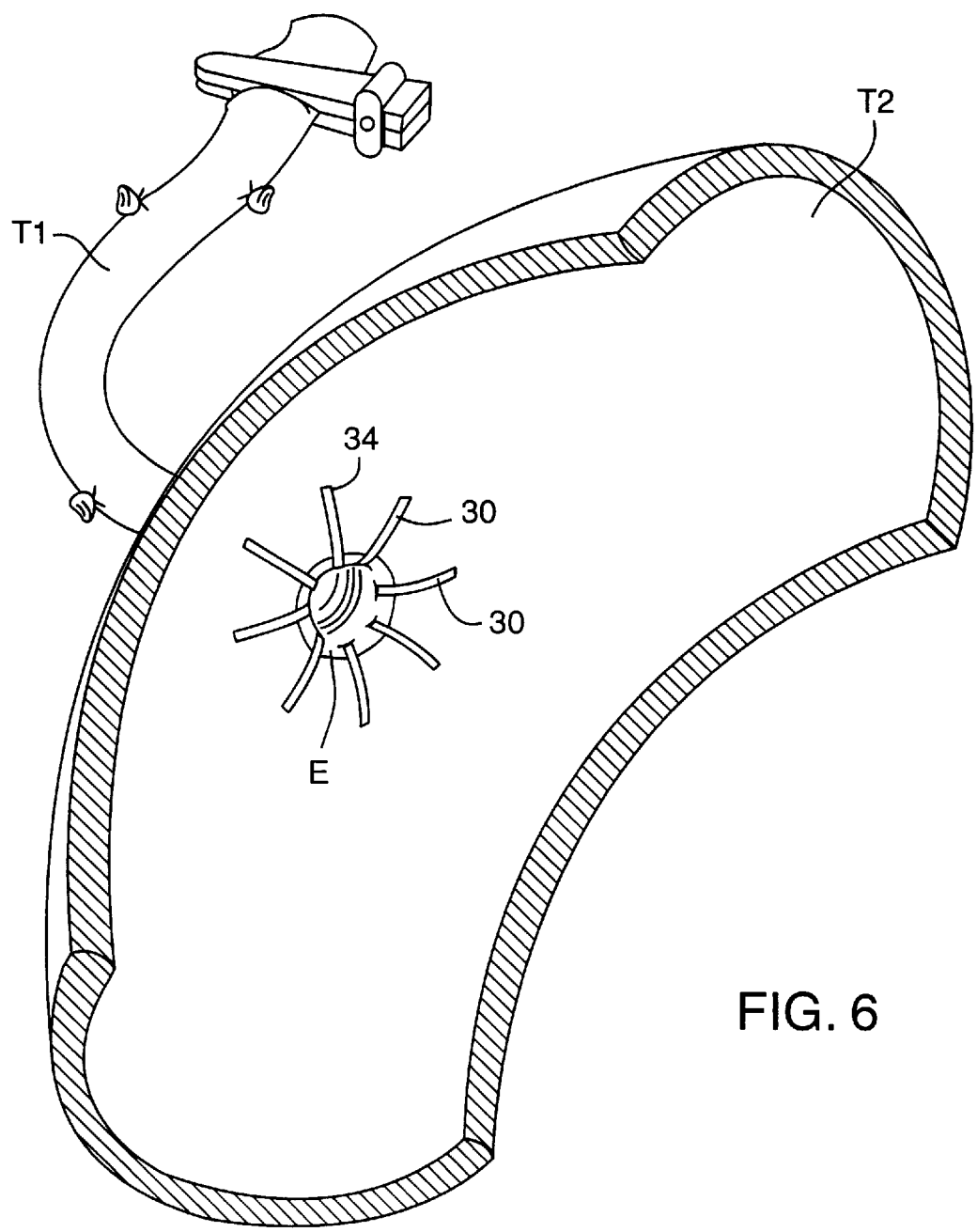
FIG. 6 is a perspective view of the anastomosis shown in FIG. 5 viewed from inside the second hollow tissue structure.

Accordingly, the anastomosis shown in FIG. 5 is formed without the tissue securing members 14 penetrating completely through the wall of the second tissue structure T2. FIG. 6 is a view from inside the second tissue structure T2 and shows the tissue securing members 14 positioned circumferentially around the opening O and the end E of the first tissue structure T1. FIG. 6 also shows the nature of the anastomosis when the invention is used in its preferred application—forming a proximal anastomosis between a vascular conduit and an aorta (wherein the distal end of the vascular conduit V is occluded by a clamp C). While the illustrated anastomosis system includes eight tissue securing members which are applied simultaneously by the applier 12, it will be appreciated that any desired number of securing members may be used.

Figure 7:
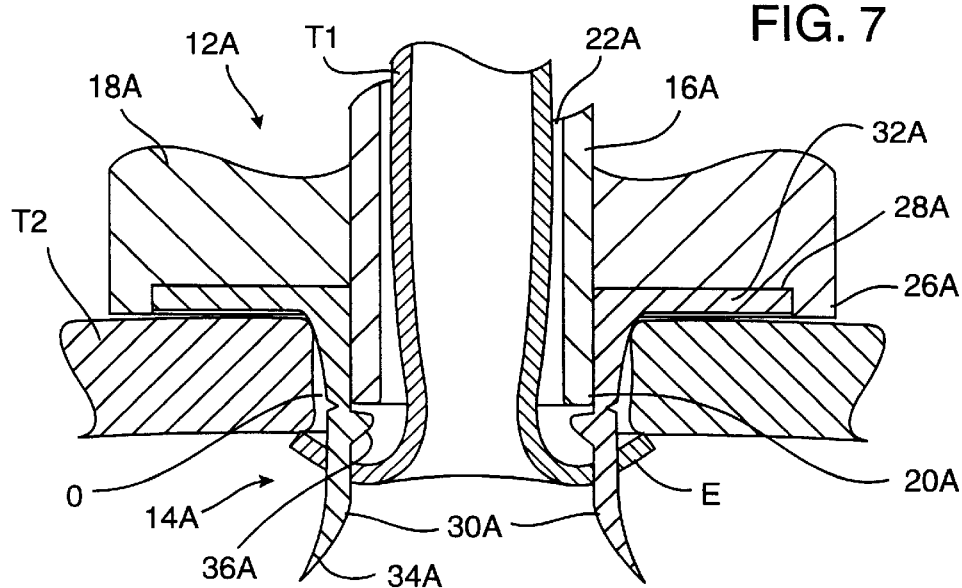
FIG. 7 is a sectional view of an applier and tissue securing members constructed according to another embodiment of the invention, the system comprising an applier loaded with tissue securing members and a first hollow tissue structure, and the applier shown positioned in an opening formed in a second hollow tissue structure.
Figure 8:
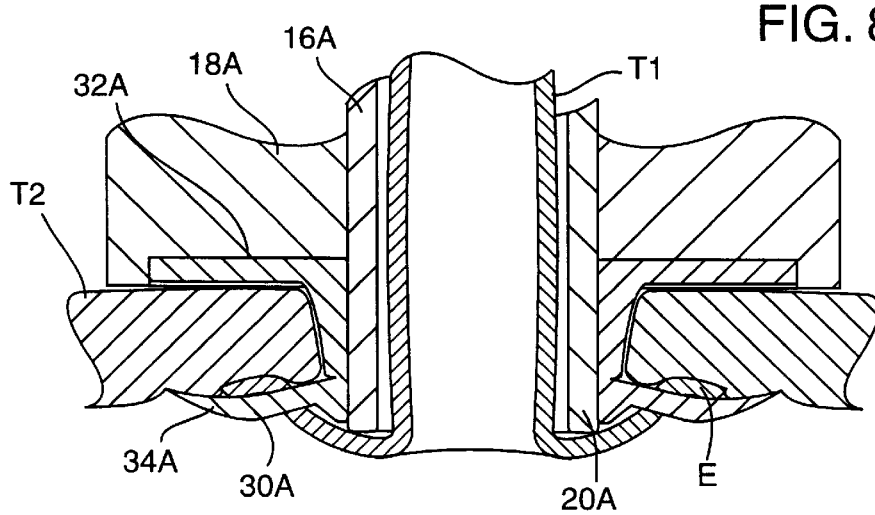
FIG. 8 is a sectional view corresponding to FIG. 8 showing the applier after it has been actuated to anastomose the first hollow tissue structure to the second hollow tissue structure.
Figure 9:
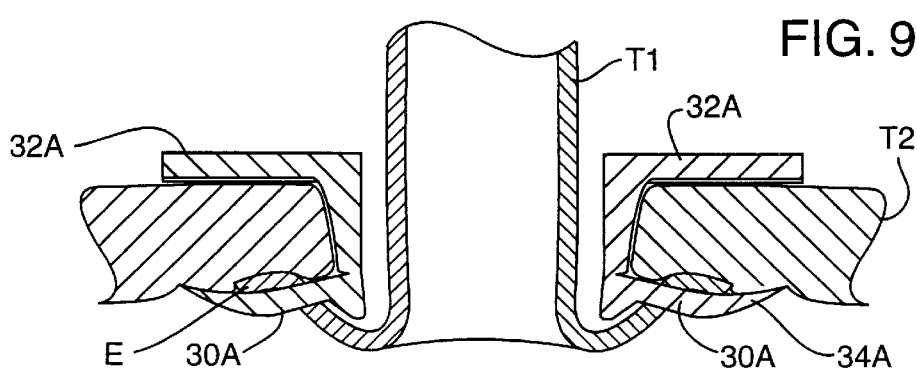
FIG. 9 is a sectional view corresponding to FIG. 8 showing the anastomosis after the applier has been removed from the hollow tissue structures.

FIGS. 7–9 illustrate an anastomosis system constructed according to another embodiment of the invention which is similar to the previous embodiment in that a plurality of tissue securing members are collapsed by an applier to secure first and second tissue structures together. This embodiment comprises an applier 12A including a first applier member 16A slidably disposed within a second applier member 18A, the applier member 16A having a bore 22A in which a first tissue structure is positioned. The second applier member 18A has a rim 26A and a surface 28A which cooperate to define a recess which receives a plurality of tissue securing members 14A.

Each securing member 14A is formed in a first, generally L-shaped configuration and comprises a first leg 30A with a tip 34A passing through the end E of the first tissue structure T1, and a second leg 32A located in the recess of the applier member 18. The members 14A are wedged between the outer surface of the applier member 16A and the rim 26A of the applier member 18A so as to be retained in the applier. The first applier member 16A has a straight end 20A (rather than a bell-shaped end) which serves to manipulate the tissue securing members 14A to their second configuration. As shown in FIG. 7, the straight end 20A of the applier member 16A is engaged with a rib 36A formed on the second leg 32A of each securing member 14A.

As shown in FIG. 8, the first leg 30A of each tissue securing members 14 is folded against the wall of the second tissue structure T2 (capturing the first tissue structure T1 therebetween) by moving the applier member 16A toward the tissue structure T2 with respect to the applier member 18A. This action causes the end 20A of the applier member 16A to drive against the rib 36A on each tissue securing member 14, which collapses the leg 30A of each member 14 against the wall of the second tissue structure T2. When the tissue securing members 14 have been collapsed completely, the ribs 36A have moved a sufficient distance to permit the applier member 16A to be removed along with the applier member 18A. The resulting anastomosis is shown in FIG. 9.

Figure 10:
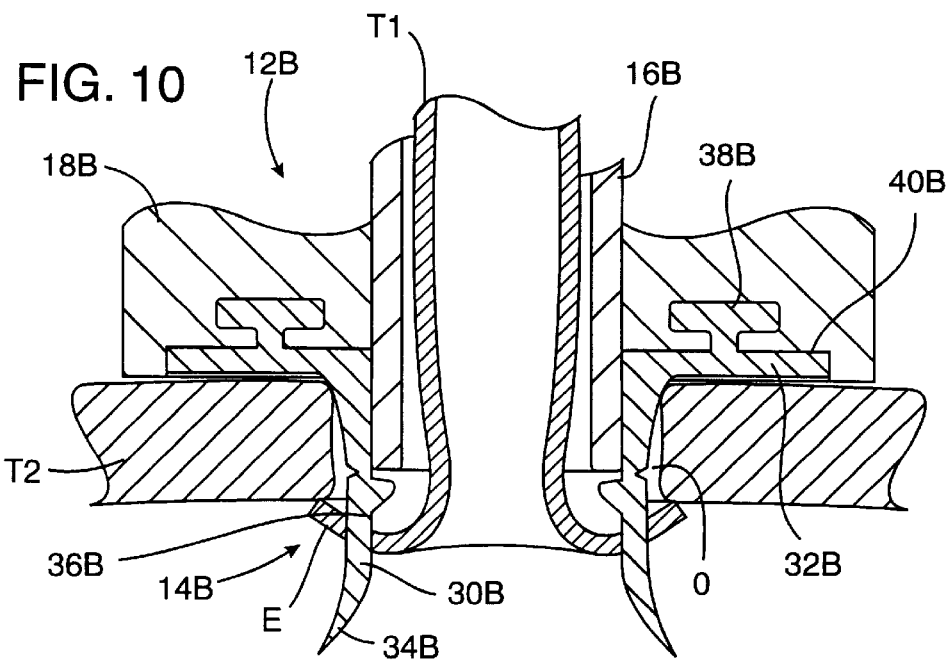
FIG. 10 is a sectional view of an anastomosis system constructed according to yet another embodiment of the invention, the system comprising an applier loaded with tissue securing members and a first hollow tissue structure, and the applier shown positioned in an opening formed in a second hollow tissue structure.
Figure 11:
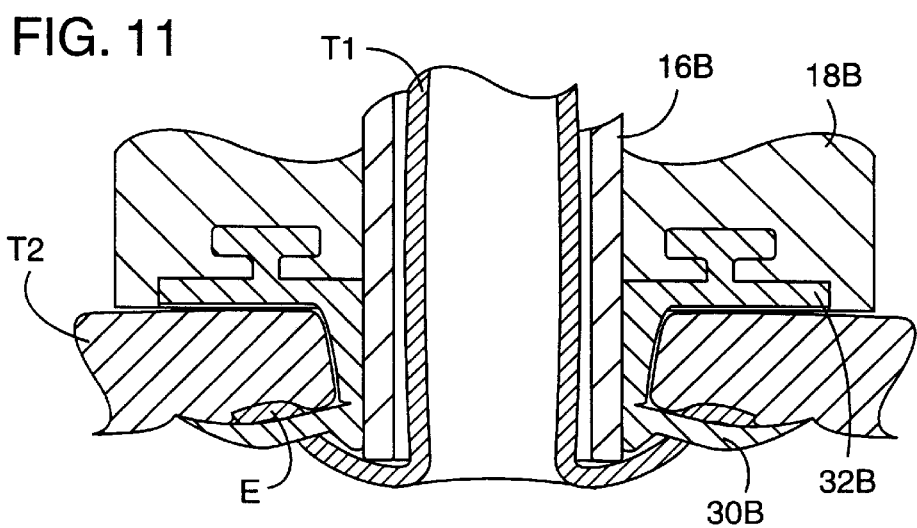
FIG. 11 is a sectional view corresponding to FIG. 10 showing the applier after it has been actuated to anastomose the first hollow tissue structure to the second hollow tissue structure.
Figure 12:
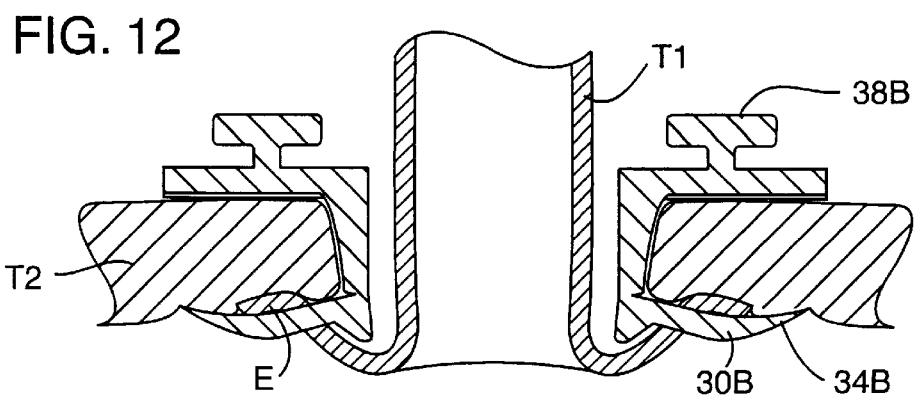
FIG. 12 is a sectional view corresponding to FIG. 11 showing the anastomosis after the applier has been removed from the hollow tissue structures.

FIGS. 10–12 illustrate an anastomosis system constructed according to another embodiment of the invention which also is similar to the previous embodiments in that a plurality of tissue securing members are collapsed against first and second tissue structures by an applier. This embodiment comprises an applier 12B which includes a first applier member 16B slidably disposed within a second applier member 18B, the applier member 16B having a bore 22B in which a first tissue structure is positioned. The applier supports a plurality of tissue securing members 14B. However, the tissue securing members 14B are supported by the applier 12B by a positive locking structure rather than compressive forces. In particular, the second leg 32B of each tissue securing member 14B is provided with a flange 38B which is received in a complementarily shaped groove 40B formed in the end surface 28B of the applier member 18B.

Actuation of the applier 12B to collapse the tissue securing members 14B into their second configuration is shown in FIG. 11 and is preferably the same as described above with respect to embodiment of FIGS. 7–9. Upon completion of such actuation, the applier members 16B, 18B are removed from the tissue securing members 14B, with the resulting anastomosis shown in FIG. 12. The end surface 28B of the second applier member 18B may be provided with open areas (not shown) that communicate with the grooves 40B so that the applier member 18B engages the flanges 38B of the tissue securing members 14B in a bayonet-type attachment, thus permitting the applier member 18B to be rotated to align the open areas with the flanges 38B and permit removal of the member 18B from the members 14B.

Figure 13:
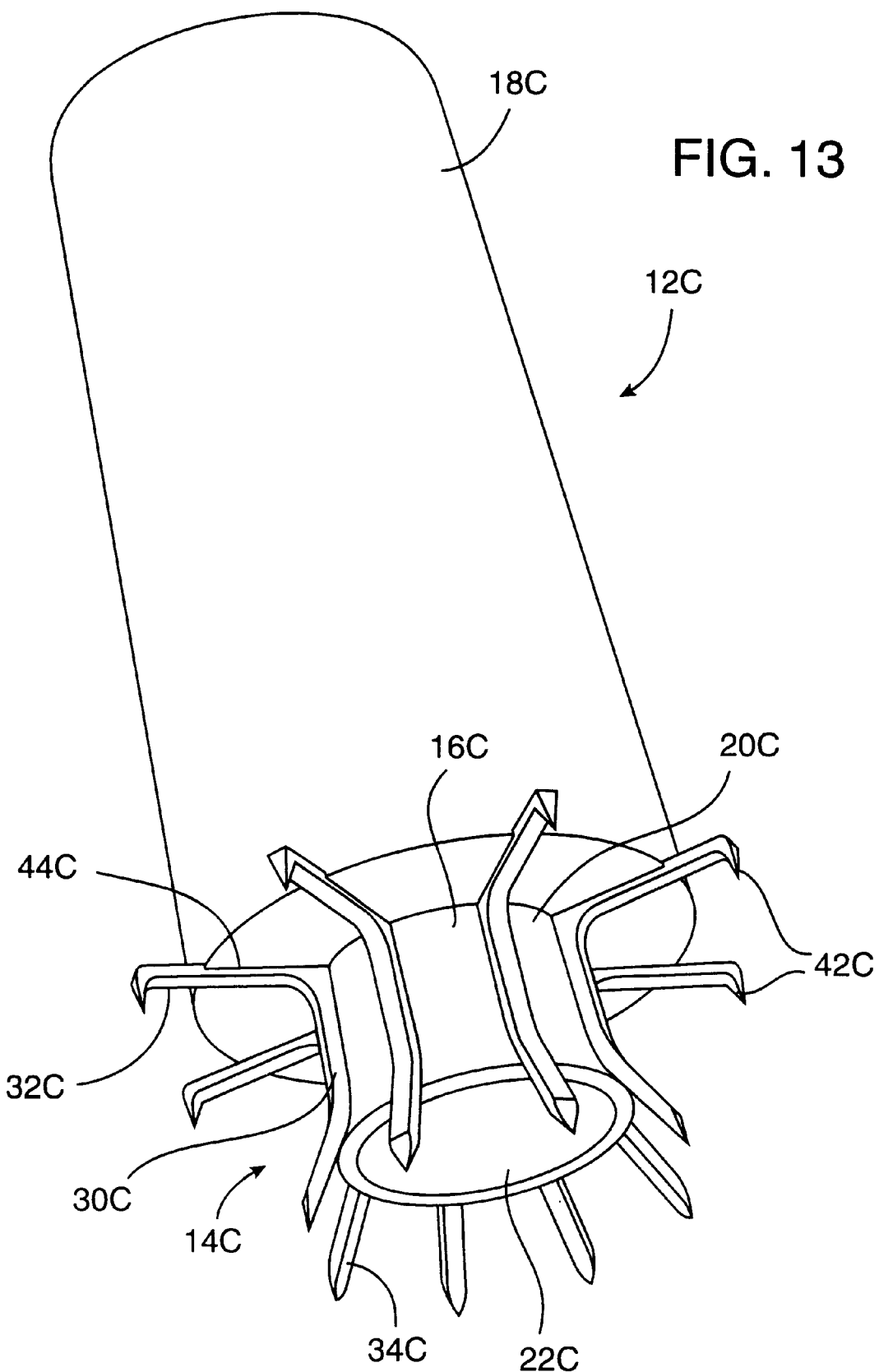
FIG. 13 is a perspective view of an anastomosis system constructed according to yet another embodiment of the invention, the system comprising an applier loaded with tissue securing members for anastomosing a first hollow tissue structure to a second hollow tissue structure.
Figure 14:
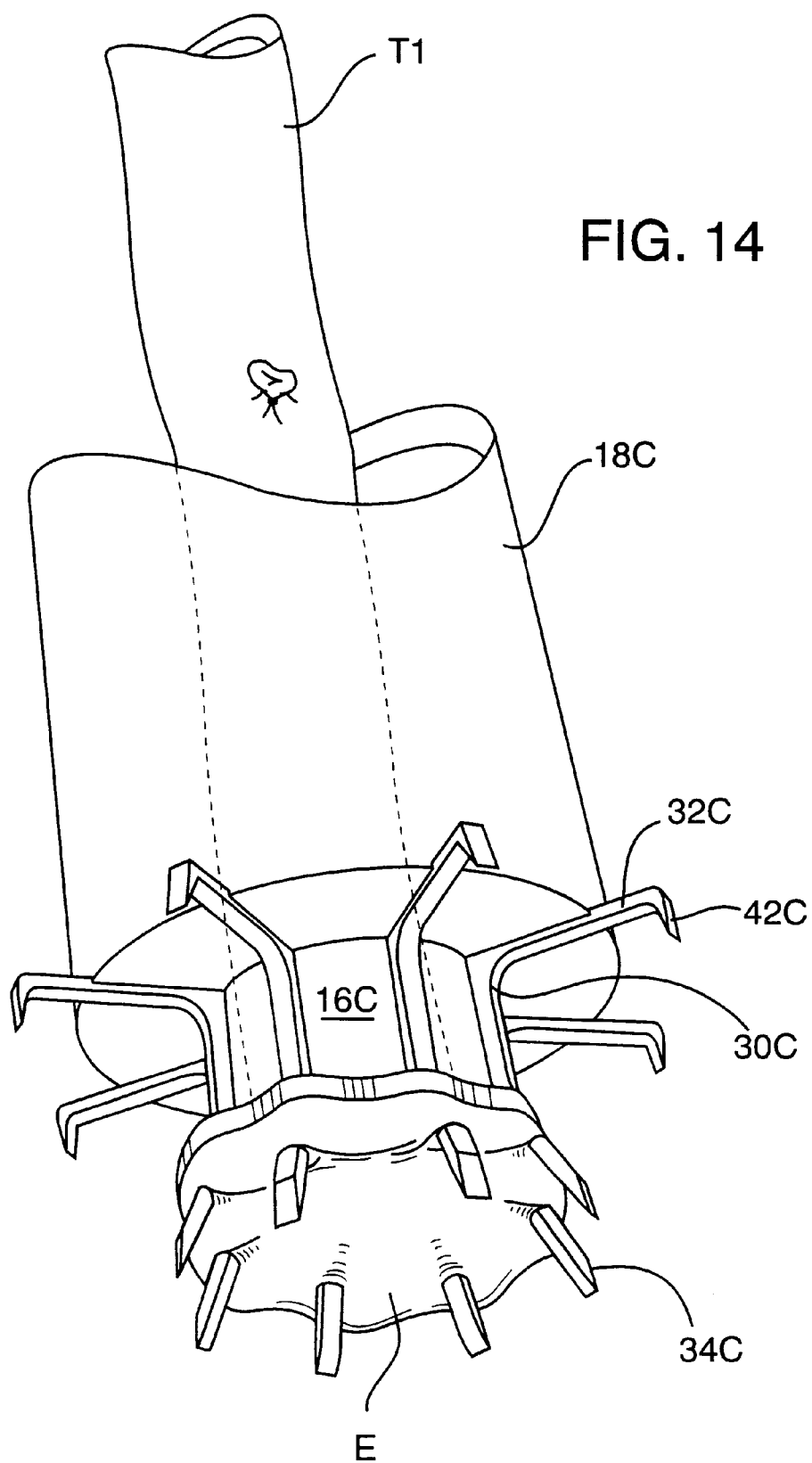
FIG. 14 is a perspective view of the device shown in FIG. 13 after a first hollow tissue structure has been loaded on the applier and engaged with the tissue securing members.
Figure 15:
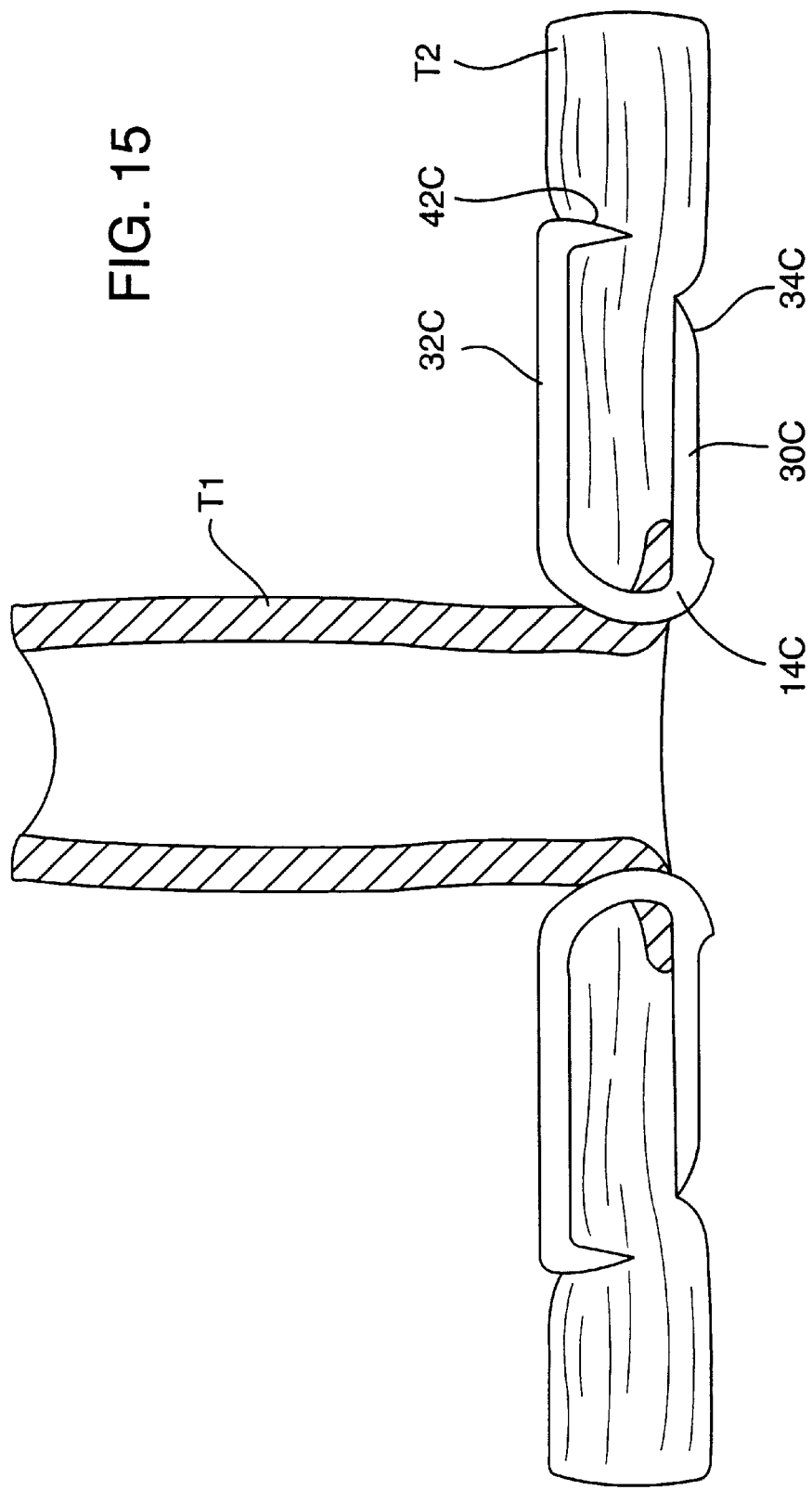
FIG. 15 is a sectional view showing the anastomosis formed between the first hollow tissue structure and a second hollow tissue structure after the applier shown in FIG. 14 has been positioned in an opening in the second hollow tissue structure, actuated, and then removed.

FIGS. 13–15 illustrate an anastomosis system constructed according to yet another embodiment of the invention which also is similar to the previous embodiments in that a plurality of tissue securing members are collapsed against respective tissue structures by an applier. This embodiment comprises an applier 12C which includes a first applier member 16C slidably disposed within a second applier member 18C, the applier member 16C having a bore 22C in which a first tissue structure is positioned. The applier members 16C, 18C support a plurality of tissue securing members 14C each of which comprises a first leg 30C and a second leg 32C. The second leg 32C terminates in an upturned, sharpened tip 42C. In addition, the applier member 18C has an end surface 28C provided with notches 44C each of which receives a second leg 32C of a tissue securing member 14C. The first leg 30C of each tissue securing member 14C abuts the applier member 16C so that the members 14C are removably supported by the applier.

As can be seen from FIG. 13, the applier member 16C has a bell-shaped end 20C which drives against the first leg 30C of each tissue securing member 14C upon moving the applier member 16C with respect to the applier member 18C, as described above in connection with the embodiment shown in FIGS. 1–6. Thus, after the end of the first tissue structure T1 has been everted over the sharpened tips 34C of each tissue securing member 14C, as shown in FIG. 14, the applier is actuated to collapse the member 14C and compress the end E of the tissue structure T1 against the interior of the wall of the tissue structure T2. As shown in FIG. 15, however, in this embodiment the tissue securing members 14C partially penetrate the second tissue structure T2 due to the sharpened tips 42C provided on the leg 32 of each member 14C. It may be desirable to partially penetrate the tissue structure T2 in order to enhance attachment of the tissue securing members to the tissue. It will be recognized that the sharpened tips 42 shown in FIGS. 13–15 are but one example of structure which may be utilized to achieve this result. Also, it will be understood that the previous embodiments may be provided with sharpened tips or other structure for partially penetrating the second tissue structure.

In each of the above embodiments, the tissue securing members pass through only one of the tissue structures and are manipulated to compress the respective tissue structures together. It is preferred that the members do not pass through the other tissue structure, though they may partially penetrate same in order to enhance locking as shown in FIG. 15. Also, while in each embodiment the tissue securing members are applied simultaneously by the applier, it will be appreciated that they may instead be applied individually. Further, while the first tissue structure is illustrated as passing through the applier, it will be understood that the applier could be configured to be passed through the tissue structure and actuated to compress or otherwise manipulate the securing members, and thereafter removed through the tissue member.

The various embodiments illustrate that the tissue securing members may be held by one or both of the applier members, and that some form of a positive locking structure may be used. In addition to the flange and groove shown in FIGS. 10–12, other structure, for example, undercuts, holes, notches, etc. may be used to temporarily attach the tissue securing members to the applier. The above embodiments also show that the applier may be actuated in various manners to manipulate the tissue securing members from the first to the second configuration. For example, the applier members may be configured to manipulate the tissue securing members on their own, or the securing members may be provided with structure to assist the action of the applier. Also, one of the applier members may be moved while the other remains stationary, or both may be moved in unison (or one after the other). It will be understood that the applier members may be moved in various directions to manipulate the tissue securing members. In addition, although the Figures illustrate the applier and tissue securing members engaging the tissue structures in a generally perpendicular manner, they could also engage the tissue structures at an angle. Finally, while the preferred embodiments are illustrated forming an end-to-side anastomosis, it will be recognized that they could also be used to form an end-to-end anastomosis.

Figure 16:
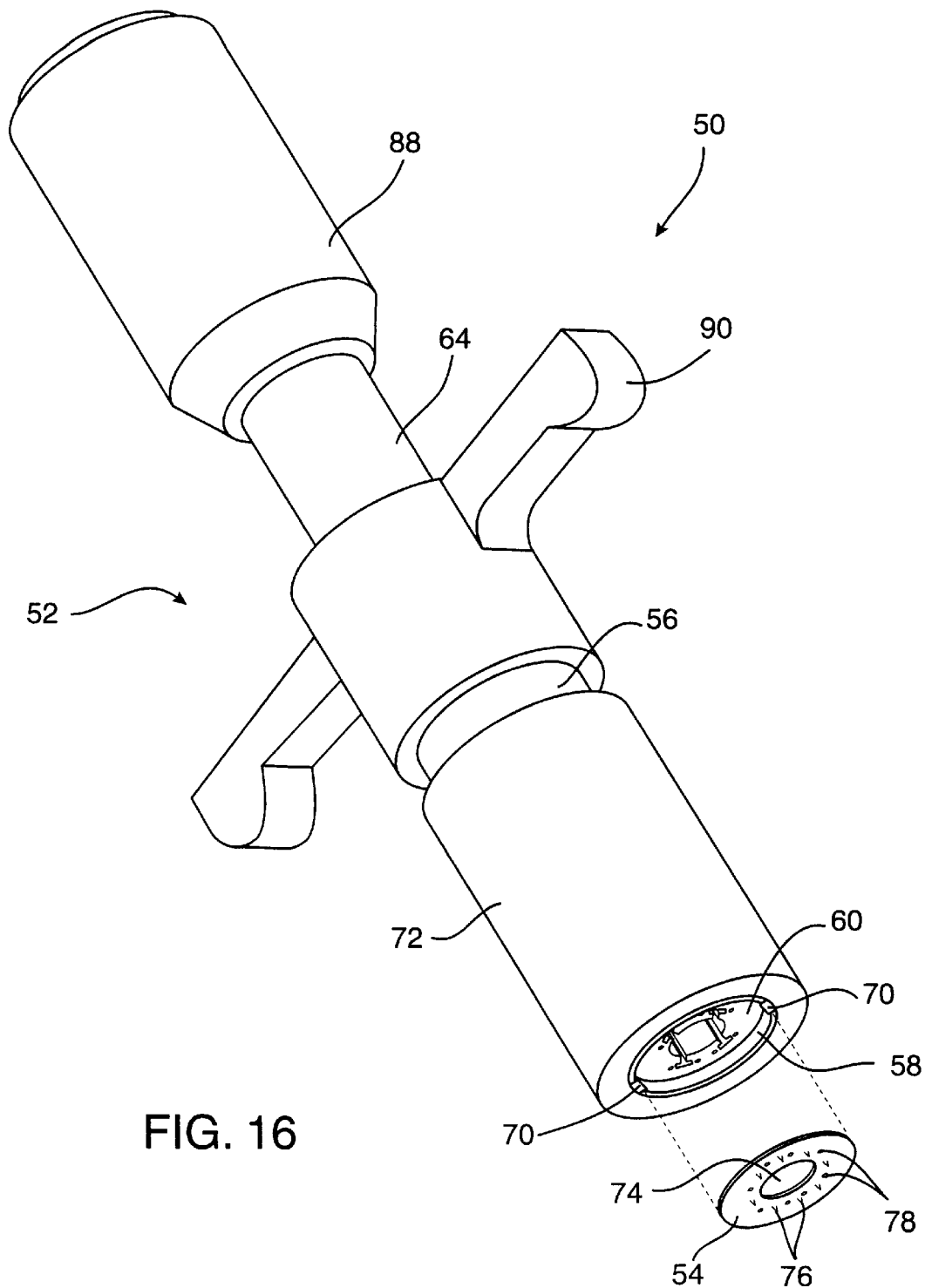
FIG. 16 is an exploded perspective view of an anastomosis system constructed according to another embodiment of the invention, the system comprising an applier and a hub for anastomosing a first hollow tissue structure to a second hollow tissue structure.

Turning now to FIGS. 16–26, an anastomosis system constructed according to another embodiment of the invention will be described. The system is designated generally by the reference numeral 50 and comprises an applier 52 in which a hub is removably mounted (FIG. 16). The applier 52 comprises a body portion 56 including a rim 58 and an end surface 60 which cooperate to define a recess that receives the hub 54. The body portion 56 is hollow and defines a bore 62 which contains a hollow plunger 64 (FIG. 22). The plunger defines a bore 66 configured to receive a first hollow tissue structure. Two spring latches 68 (FIG. 23) are located on the outer surface of the body portion 56 and have ends 70 which engage the periphery of the hub 54 to hold it in the recess against the rim 58. A sleeve 72 is slidably disposed on the body portion 56 and, when in a forward position as shown in FIG. 16, biases the spring latches 68 inwardly to hold the hub 54 on the applier 52.

The preferred hub 54 is disc-shaped and has a central opening 74 which receives the first tissue structure; however, as discussed below, the hub may take various forms. A plurality of barbs 76 (or similar structure) is provided on the surface of the hub 54 for engaging the end of the first tissue structure. A plurality of openings 78 are formed in the hub 54 for receiving a plurality of tissue securing members which pass through the first tissue structure and engage a second hollow tissue structure.

Figure 17:
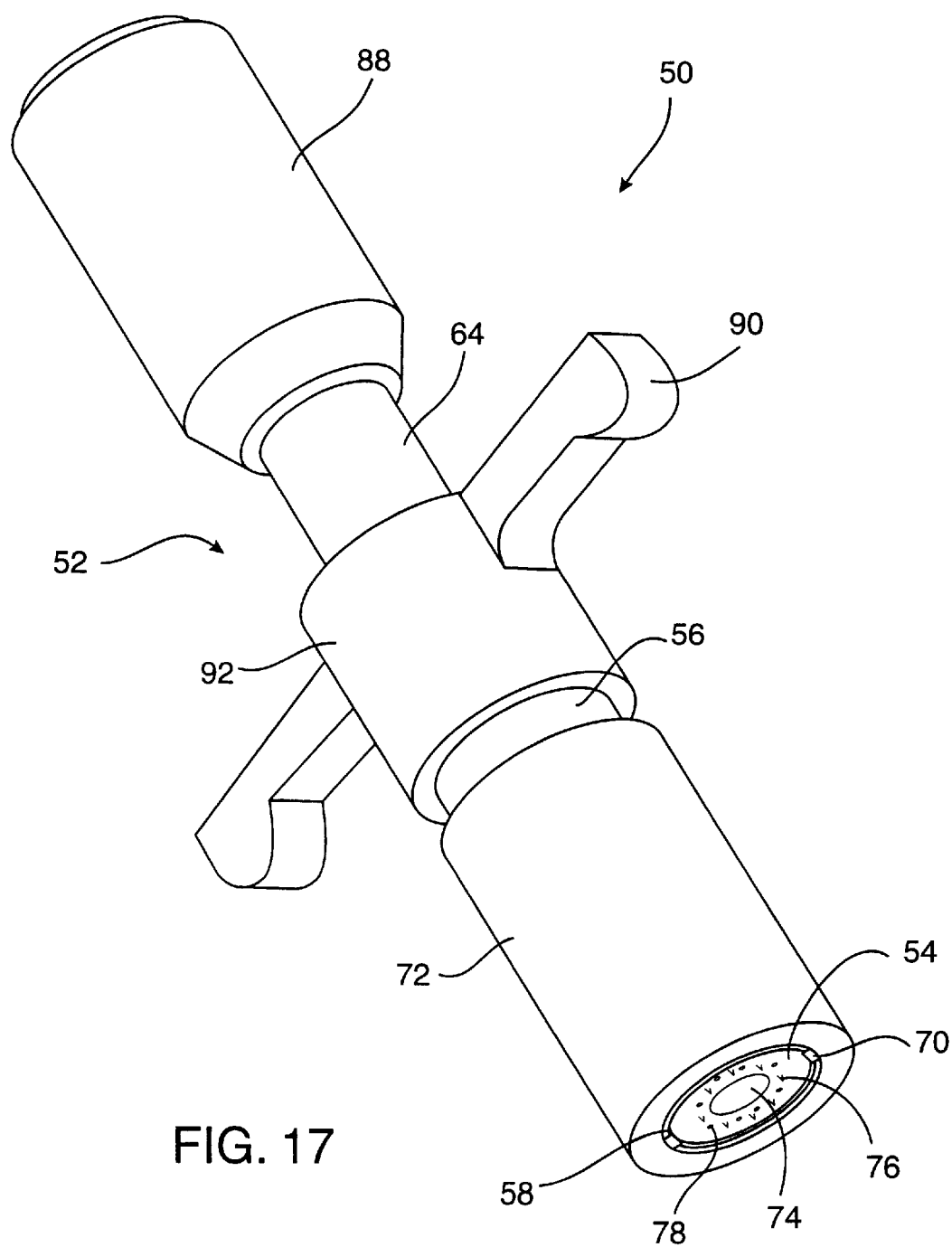
FIG. 17 is a perspective view of the anastomosis system shown in FIG. 16 with the hub loaded on the applier.
Figure 18:
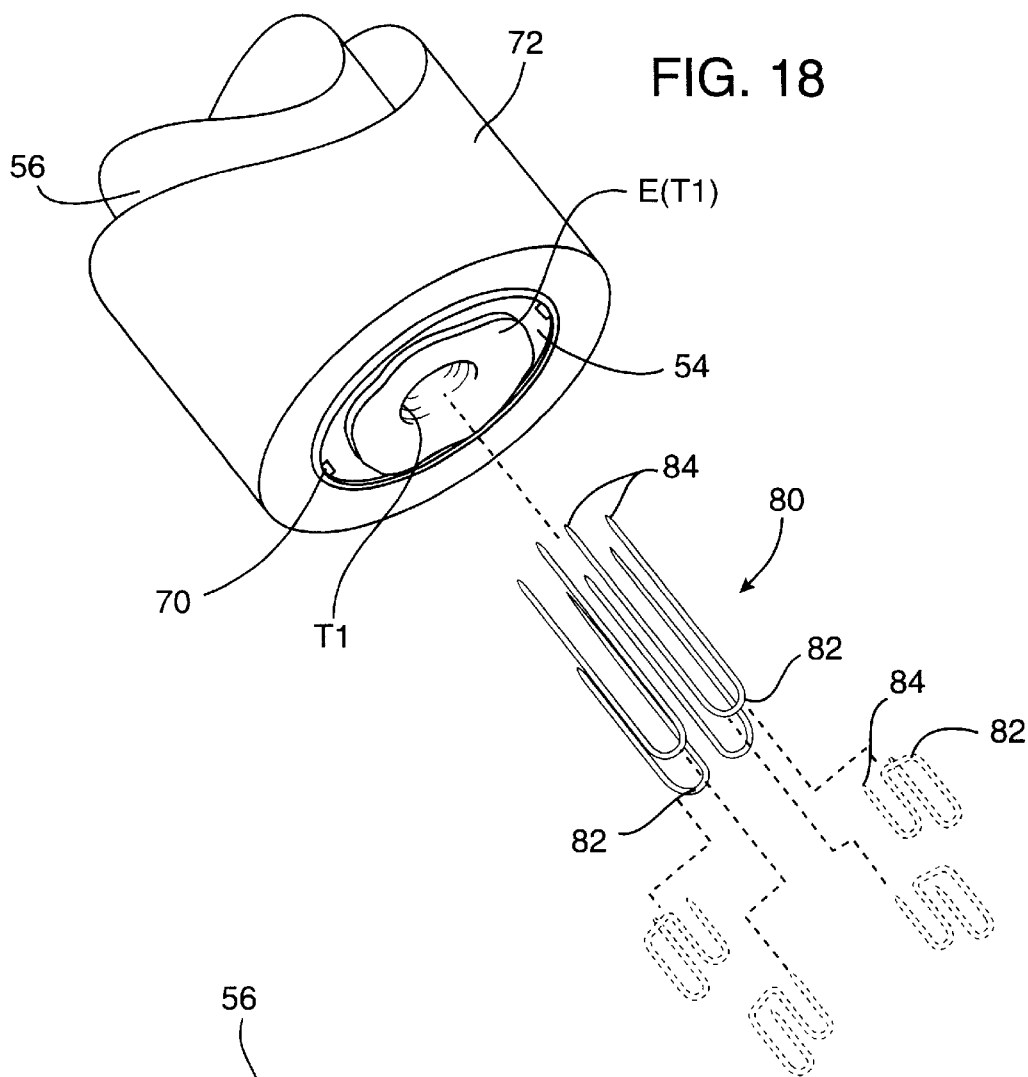
FIG. 18 is a perspective view of the system shown in FIG. 17 after a first hollow tissue structure has been loaded on the applier and hub, with tissue securing members exploded from the applier.

With the hub 54 is positioned in the recess in the body portion 56 of the applier, as shown in FIG. 17, the first tissue structure T1 is threaded through the bore 62 and through the bore 66 in the plunger 64 until the end of the tissue structure extends slightly beyond the hub 54. For example, a snare (not shown) may be used to grasp the tissue structure T1 as described in connection with the embodiments discussed above. The end of the first tissue structure T1 is then everted and pressed onto the barbs 76, the resulting configuration being shown in FIG. 18. The end E of the first tissue structure T1 is shown everted approximately 90°, although it may be everted more or less than 90°.

Next, a plurality of tissue securing members a repassed through the end E of the first tissue structure T1 and through the openings 78 in the hub 54. The preferred tissue securing members comprise hooks 80 (FIG. 19) each of which is U-shaped and has a closed end 82 and sharpened ends 84. In one preferred embodiment, the hooks 84 are formed of a strong, highly resilient material, for example, stainless steel or a superelastic material such as nitinol. Each hook 80 is formed in a first configuration, shown in phantom in FIG. 18, which is generally C-shaped with the closed end 82 adjacent to the sharpened end s 84. The hooks 80 are biased from the first configuration to a second configuration, shown in solid in FIG. 18, which is generally straight. The hooks 80 are preferably preloaded on a cartridge (not shown) having openings which receive the closed ends 82 of the hooks and maintain them in the second configuration. The cartridge preferably is provided with a mechanism for ejecting the hooks 80. Thus, the cartridge is positioned against the applier 52 with the sharpened ends 84 of the hooks 80 aligned with the openings 78 in the hub 54, the cartridge preferably including structure or and indicator to aid in aligning the hooks 80 and the openings 78 in the hub.

Figure 19:
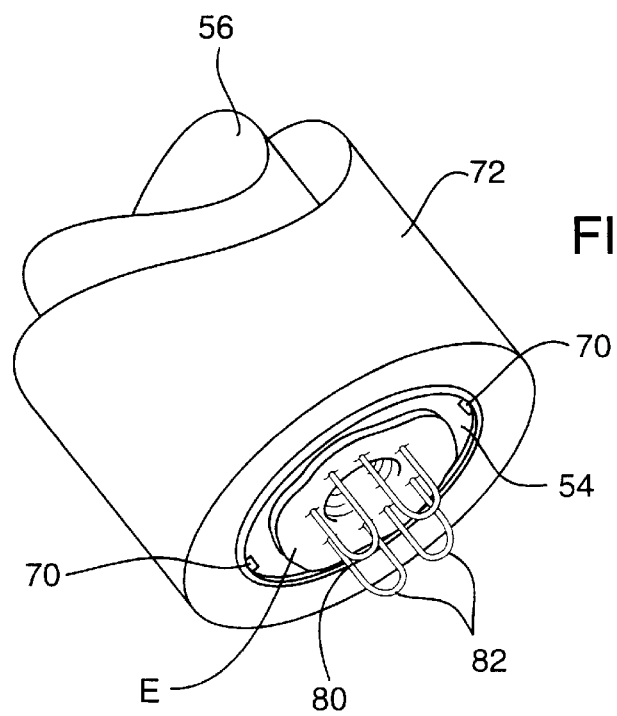
FIG. 19 is a perspective view of the system shown in FIG. 18 after the tissue securing members have been engaged with the first hollow tissue structure and loaded on the applier and hub.
Figure 20:
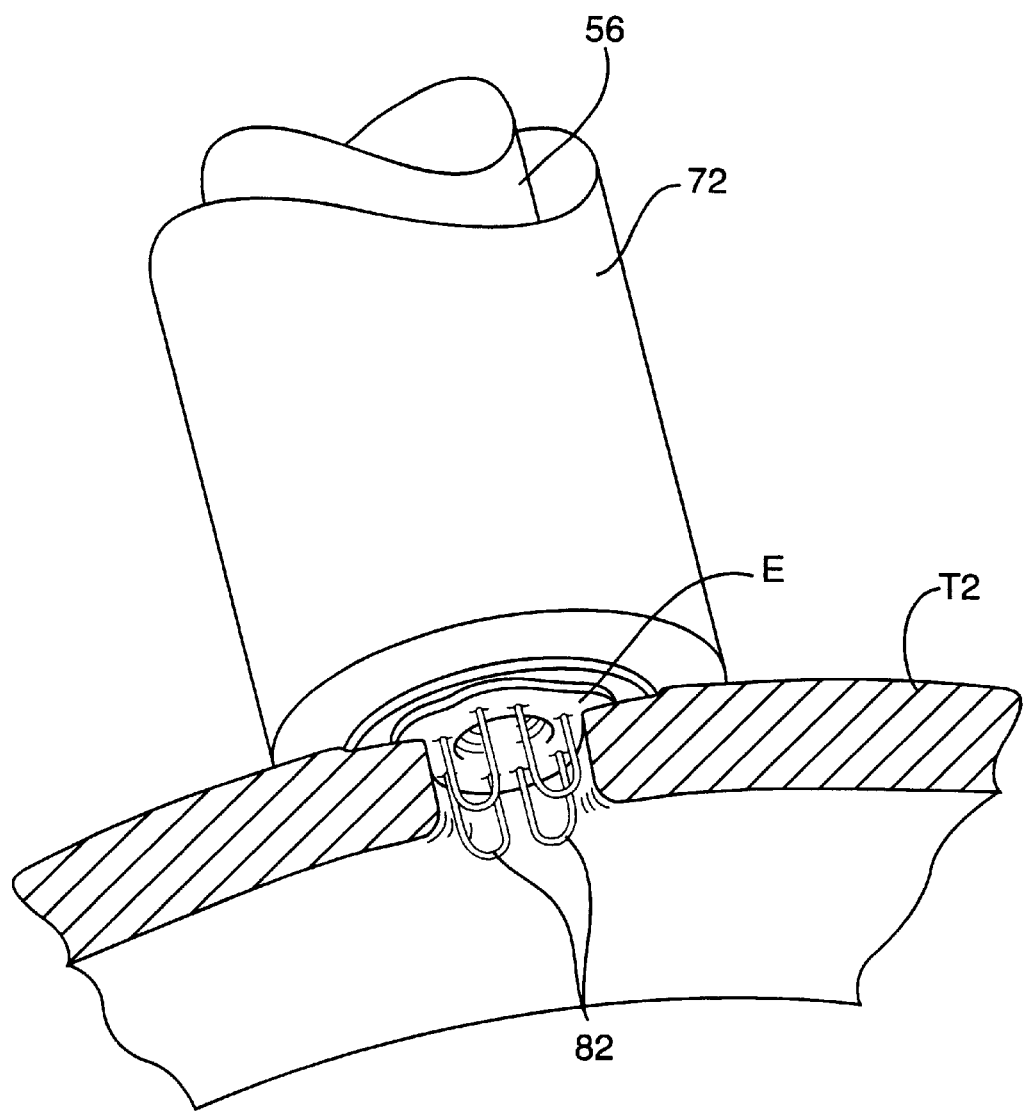
FIG. 20 is a perspective view of the system shown in FIG. 19 after the applier, hub, first hollow tissue structure, and tissue securing members have been positioned in an opening formed in the second hollow tissue structure.

The cartridge is actuated to eject the hooks so as to force the sharpened ends 84 through the end E of the first tissue structure T1 and through the openings 78 in the hub 54. The resulting configuration is shown in FIG. 19. The hooks 80 are held in the applier 52 and possess a considerable amount of stored energy due to their being manipulated from the first to the second configuration. Next, the applier is positioned against the second tissue structure T2 so that the hooks 80 extend through an opening O formed therein, and the end E of the first tissue structure T1 is pressed against the outer surface of the wall of the tissue structure T2. This configuration is shown in FIG. 20. The applier 52 is now ready to be actuated to secure the first and second hollow tissue structures together to form the anastomosis.

Figure 21A:
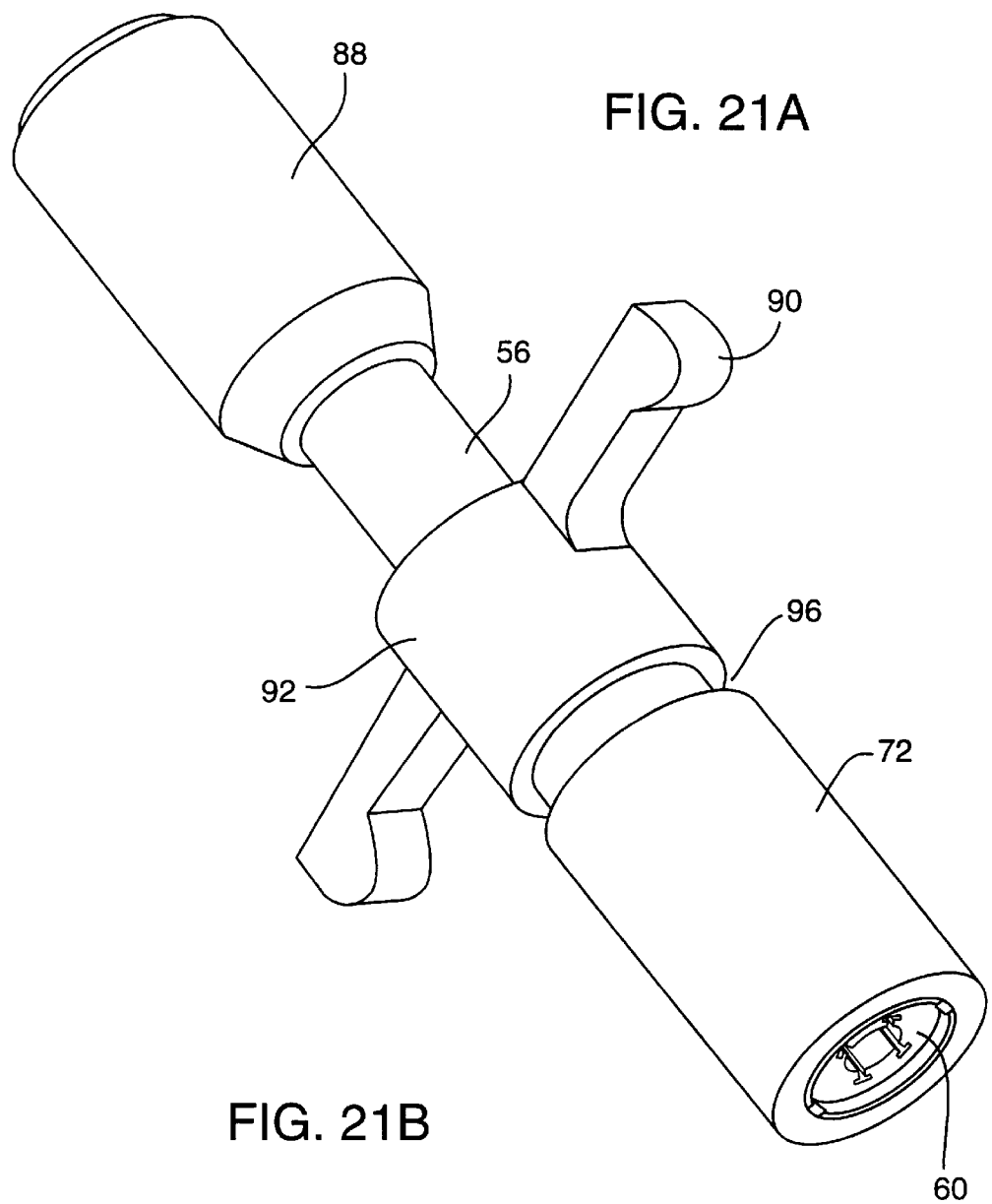
FIG. 21 is a perspective view of the applier shown in FIG. 16 in a first stage of actuation.
Figure 21B:
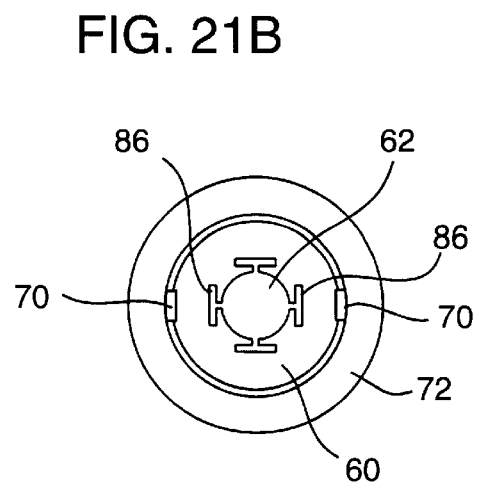
Figure 22A:
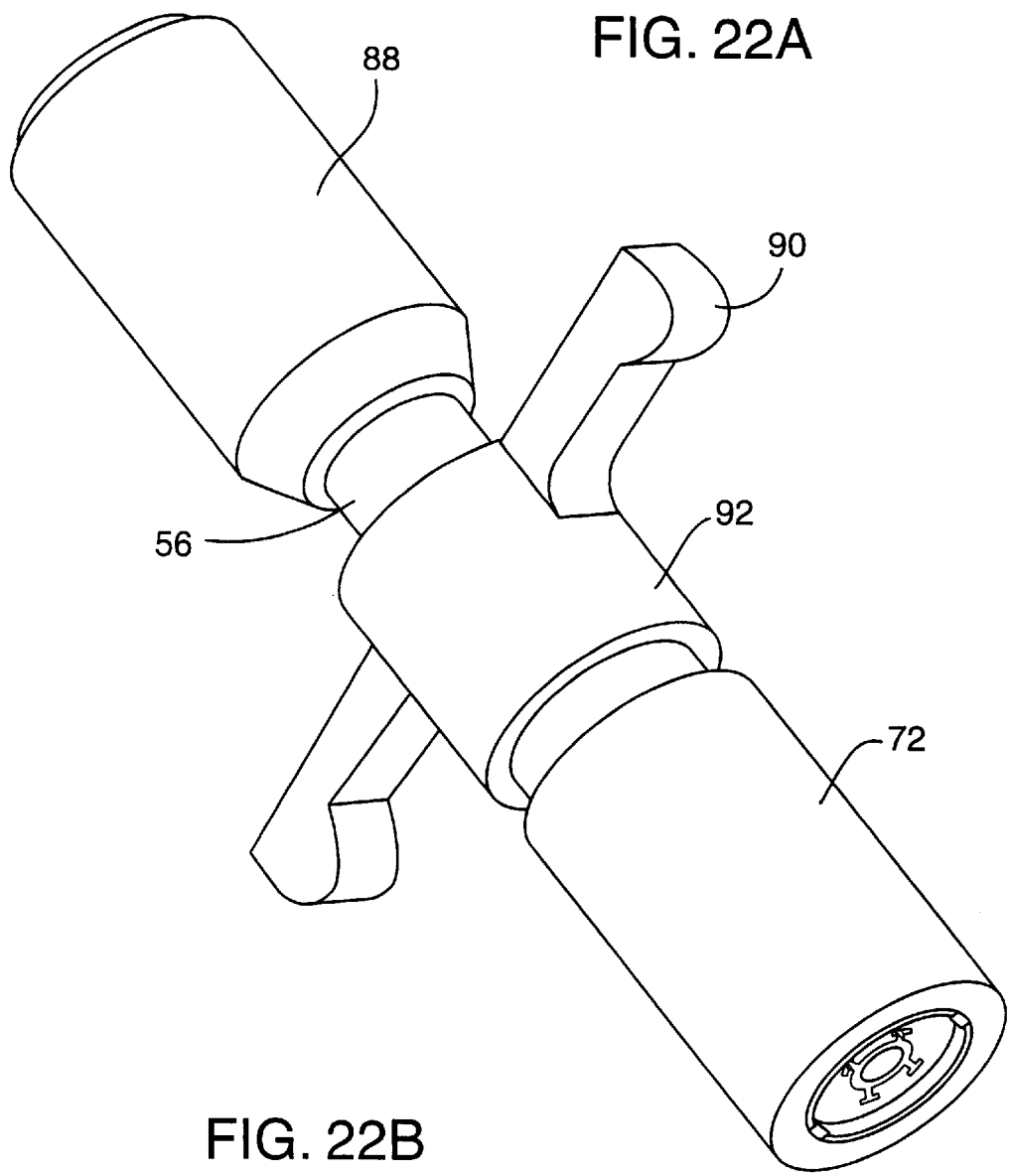
FIG. 22 is a perspective view of the applier shown in FIG. 21 in a second stage of actuation.
Figure 22B:
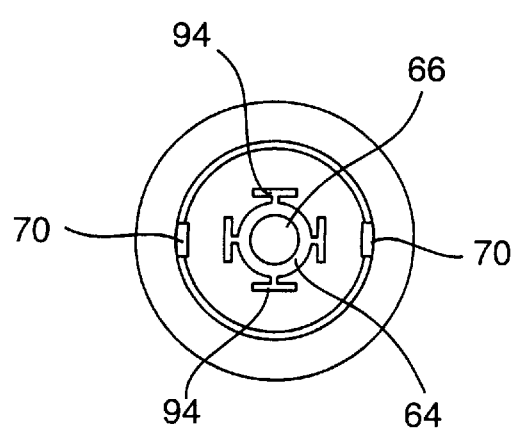

Operation of the applier 52 will be described with particular reference to FIGS. 21A–23B, which illustrate the applier 52 without the hub 54 or first tissue structure T1 for purposes of explanation. FIG. 21A shows the applier 52 in its initial configuration prior to loading of the hub 54 and the first tissue structure T1. FIG. 21B is an end view of the actuator in this configuration. As can be seen from these Figures, the bore 62 in the body portion 56 of the applier is provided with a plurality of slots 86 around its periphery, each slot 86 corresponding to one of the hooks 80. Thus, when the hooks 80 are loaded onto the applier they pass through the end E of the first tissue structure T1, through the openings 78 in the hub 54, and into the slots 86. As such, the slots 86 hold the hooks 80 in their second configuration and prevent them from returning to their first configuration.

The applier 52 is actuated by depressing the end 88 of the plunger 64, which may be performed by grasping extensions 90 of a collar 92 with two fingers and pressing the end 88 with the thumb. This results in the configuration shown in FIGS. 22A and 22B, wherein the plunger 64 has moved forward to a point where it is flush with the end surface 60 of the body portion 56. The plunger 64 comprises a tubular body with extensions 94 having a shape complementary to the slots 86 in the body portion 56. As the plunger 64 moves forward, the extensions 94 slide forward within the slots 86. The extensions 94 contact the sharpened points 84 of the hooks 80 to force the hooks 80 out the slots 86. The hooks 80 are then free to assume their first configuration (shown in phantom in FIG. 18) which results in the closed ends 82 of the hooks turning outward and clamping against the interior surface of the second tissue structure T2 (as shown in FIG. 24).

Figure 23A:
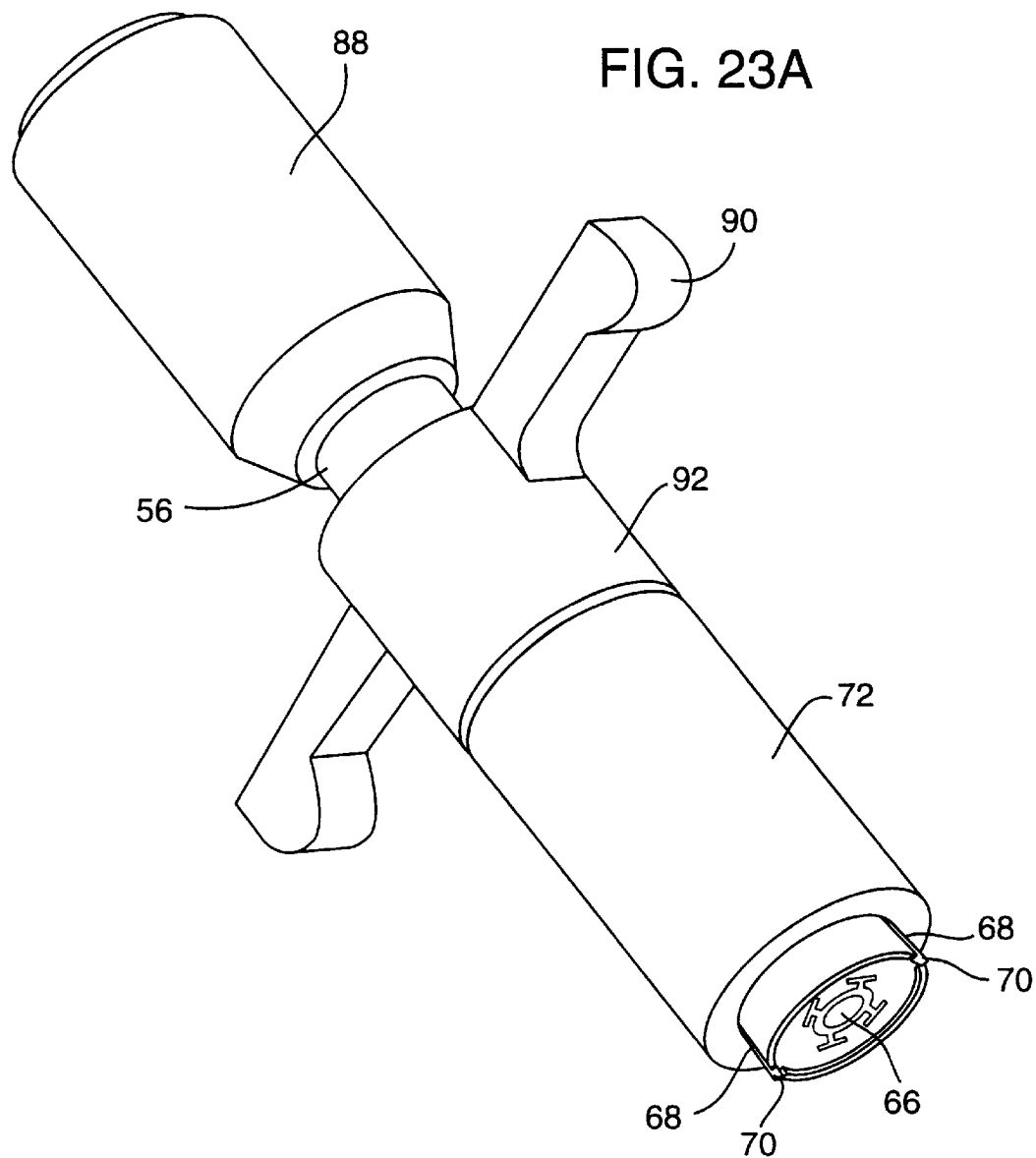
FIG. 23 is a perspective view of the applier shown in FIG. 22 in a third stage of actuation.
Figure 23B:
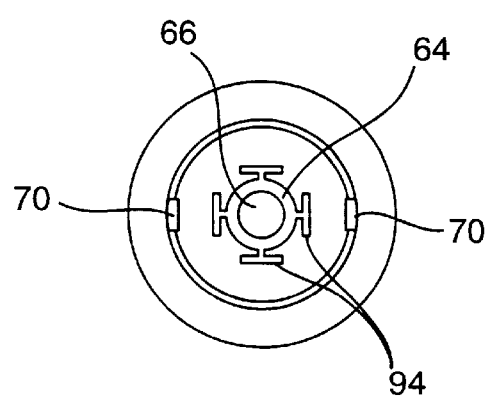

Next, referring to FIGS. 23A and 23B, the sleeve 72 is retracted away from the second tissue structure T2 which allows spring latches 68 to move radially outward so that the ends 70 thereof disengage the periphery of the hub 54. The applier 52 may then be removed from the second tissue structure T2 which releases the sharpened ends 84 of the hooks 80 so that they spring outward into clamping contact with the hub 54 and/or the exterior surface of the tissue structure T2. Before the sleeve 72 is retracted, it is in the position shown in FIGS. 21A and 22A. In this position the sleeve 72 is spaced from the collar 92 by a gap 96. A mechanism may be provided to selectively lock the sleeve 72 in the forward position until it is desired to move the sleeve forward. For example, a ring (not shown) may be positioned in the gap 96 and then removed to slide the sleeve 72 to the position shown in FIG. 23A.

Figure 24:
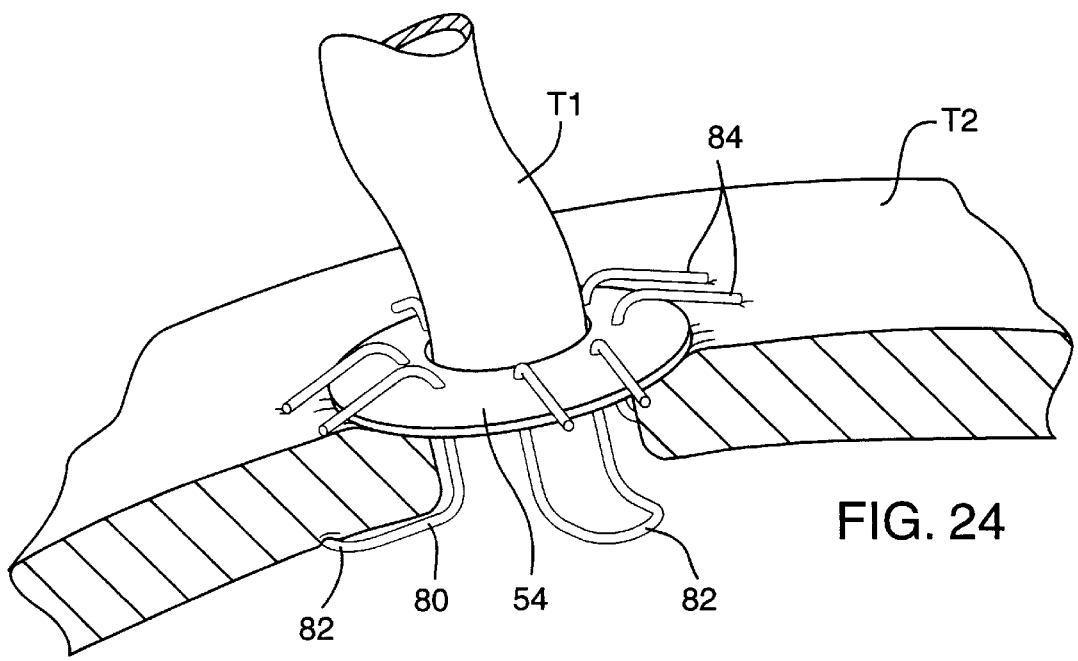
FIG. 24 is a perspective view corresponding to FIG. 20, partially in section, showing the anastomosis after the applier has been actuated to apply the hub and tissue securing members and then removed.
Figure 25:
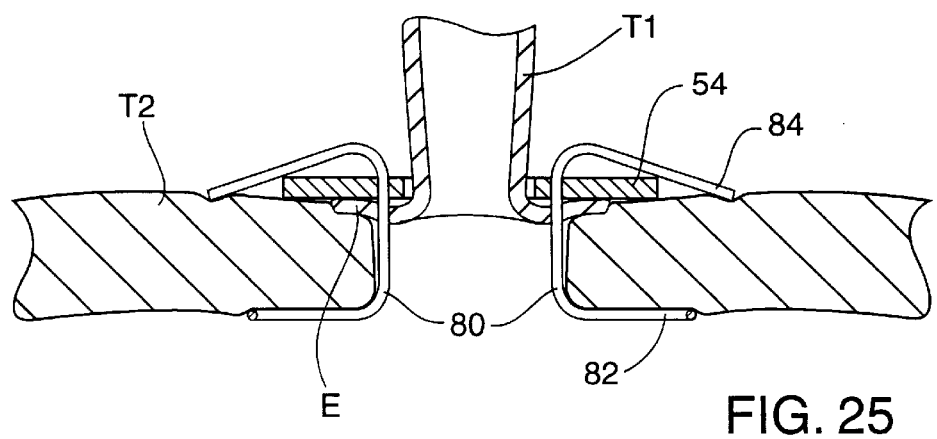
FIG. 25 is a sectional view of the anastomosis shown in FIG. 24.
Figure 26:
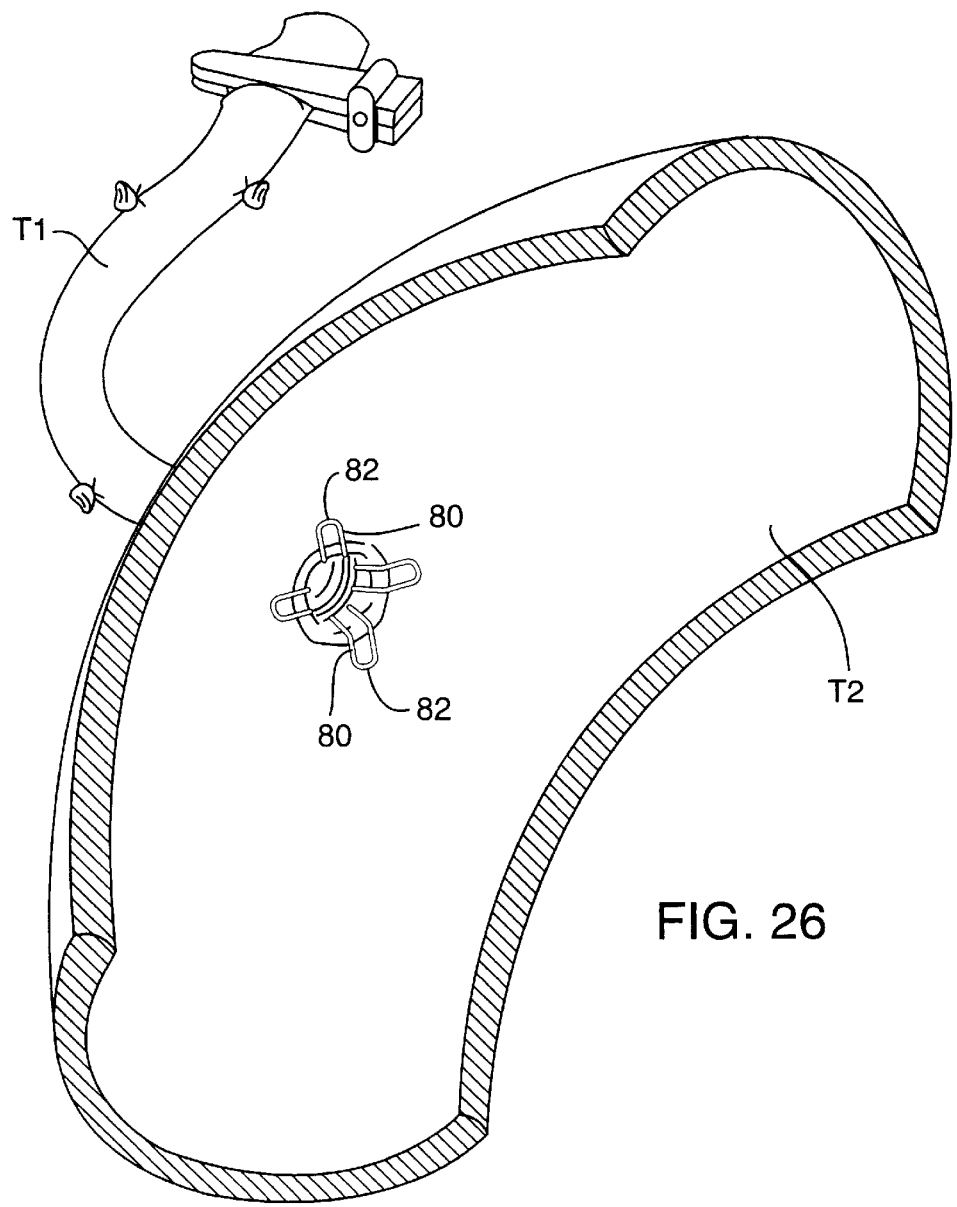
FIG. 26 is a perspective view of the anastomosis shown in FIGS. 24 and 25 viewed from inside the second hollow tissue structure.

FIGS. 24–26 show the resulting anastomosis formed by the system illustrated in FIGS. 16–23. As can be seen, the hooks 80 try to return to their unbiased configuration and in doing so exert considerable compressive force to sandwich the everted end E of the first tissue structure T1 between the hub 54 and the second tissue structure T2, thereby providing a secure, fluid tight anastomosis. While FIGS. 24 and 25 show the sharpened ends 84 of the hooks 80 engaging the second tissue structure T2, in some embodiments the hub 54 will have a thickness which prevents such engagement. These embodiments also produce a secure anastomosis due to the force exerted by the hooks 80 on the hub 54, which in turn exerts force against the end E of the first tissue structure T1. This force, coupled with the force exerted against the interior surface of the second tissue structure T2, ensures that anastomosis is secure while providing fluid communication between the two tissue structures.

The hub 54 is preferably formed of stainless steel, a resilient polymer, or other suitable implantable materials, while the hooks 14 are formed of stainless steel, titanium, or other implantable materials.

Figure 27:
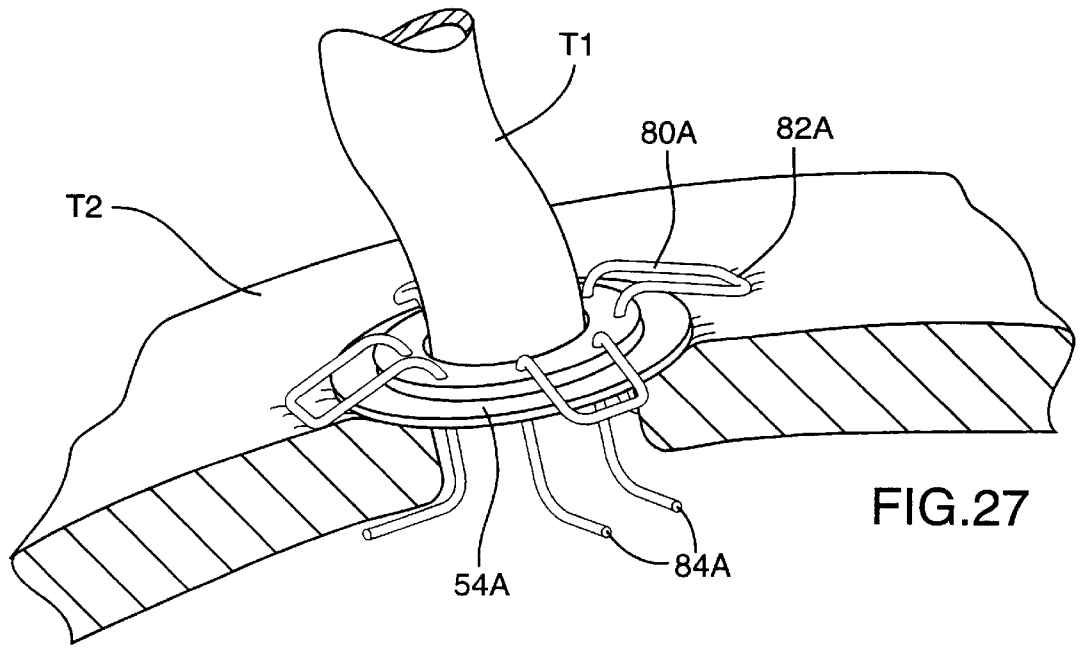
FIG. 27 is a perspective view of an anastomosis including a hub constructed according to another embodiment of the invention, and wherein the tissue securing members are positioned differently than in the previous embodiments.

FIG. 27 shows an additional embodiment of an anastomosis device comprising a hub 54A which includes an enlarged central portion 98. This hub design may be desirable in applications requiring additional rigidity, or when it is desired to space the hooks 80A from the exterior surface of the second tissue structure T2. In addition, in the embodiment of FIG. 27, the hooks 80A are reversed from the orientation used in FIGS. 16–26. That is, the closed ends 82A are positioned on the exterior of the second tissue structure T2 and the sharpened ends 84A are positioned on the interior of the second tissue structure T2. If the anastomosis device of the invention is used in this configuration, the hooks 80A can be preloaded on the applier with the closed ends 82A disposed in the slots 86 of the bore 62 in the body portion 56 of the applier. The sharpened ends 84 thus would extend upward to allow the hub 54A and the end E of the first tissue structure T1 to be engaged with the hooks 80A. As such, in this embodiment a separate device preloaded with the hooks would not be required to place the hooks in the applier.

Figure 28:
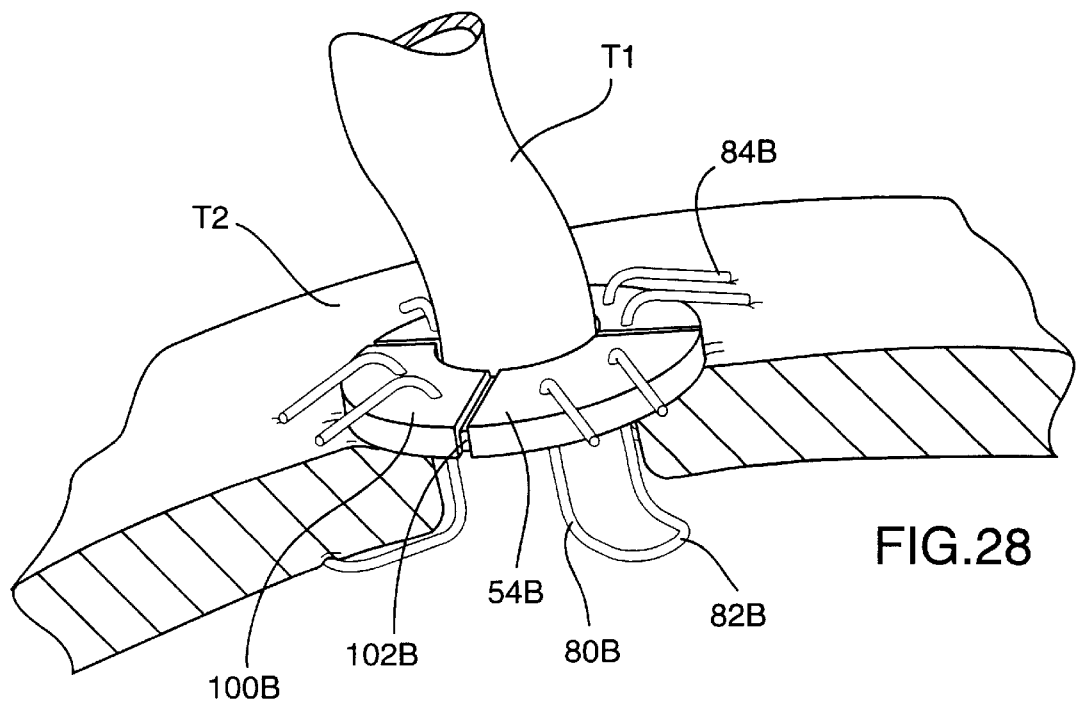
FIG. 28 is a perspective view of an anastomosis including a hub constructed according to yet another embodiment of the invention.

FIG. 28 shows another embodiment of an anastomosis device comprising a hub 54B which comprises discrete segments 100B each configured to receive and support a hook 80B. Each of the hub segments 100B has a pair of openings for receiving the legs of a hook 80B which first pass through the everted end E of the first tissue structure T1. The hub segments 100B preferably are joined to each other by a compliant member 102B which permits relative movement between adjacent hub segments. This feature provides flexibility in positioning of the hub with respect to the hooks 80B. Thus, it is not necessary to precisely align the hub and the hooks in order to engage the components. In addition, once the anastomosis has been formed and blood flow through the hollow tissue structures resumes and the pressure increases, the hub may expand to follow the contour of the tissue interface. The compliant member 102B is preferably made of a resilient, biocompatible material such as silicone, ePTFE, surgical gauze or fabric, etc. As an alternative to joining the hub segments 100B to each other by compliant members 102B, the segments could instead be secured to a washer-like member (not shown) having an opening generally aligned with the opening in the hub 54B. The washer-like member is preferably made of the same material as the compliant members 102B so as to permit relative movement of the hub segments. Additionally, it should be understood that the hub may comprise separate, discreet segments that are not attached by a compliant member but are secured to the tissue only by the hooks.

Referring to FIGS. 29A–30B, two embodiments of an anastomosis device constructed according to another aspect of the invention will be described. In these embodiments, a hub 110 receives and supports hooks 112. The hooks 112 are formed of a rigid material and thus, unlike the previous embodiments, are not manipulated from an initial configuration to a second configuration in order to store energy that is later used to apply a compressive force to the tissue structures. The hooks 112, however, are engaged with the first tissue structure T1 and are also positioned in the second tissue structure T2 in a first configuration. The hooks are then manipulated to a second configuration to secure the tissue structures together.

In the embodiment shown in FIGS. 29A and 29B, each hook 112 is generally L-shaped and has one leg that is passed through an opening in the hub 110 and the everted end E of the first tissue structure T1. The hub 110, hooks 112 and end E of the first tissue structure T1 are positioned against the exterior surface of the second tissue structure T2 by an applier (not shown) to the position of FIG. 29A. From this position, the applier is actuated to rotate the hooks 112 in the direction of the arrows approximately 90° to move the hooks from the first configuration to a second configuration in which the other leg of each hook is clamped against the interior surface of the second tissue structure T2, as shown in FIG. 29B. In the embodiment of FIGS. 30A and 30B, one leg of each of a plurality of L-shaped hooks 112A is passed through the hub 110A and the everted end E of the first tissue structure T1. An applier (not shown) may be used to position the hub 110A and hooks 112A as shown in FIG. 30A, and then actuated to rotate the hooks in the direction of the arrows to position the other legs of the hooks under the second tissue structure T2. The hooks 112, 112A are preferably formed of stainless steel or other suitable implantable materials. The hub It is desirable in these embodiments to tension the hooks in order to increase the compressive force exerted against the tissue structures and ensure a secure, fluid tight anastomosis. Any suitable tensioning means may be used. For example, a spring may be provided on the hub to bias the hooks away from the second tissue structure T2, thereby clamping the tissue structures. Alternatively, the hooks may be tensioned and then held in place with respect to the hub by a lock nut or other fastener, the nut being held on the hook by friction or a positive locking engagement. Further, each hook may be tensioned and then the portion thereof that is located outside the second tissue structure T2 severed to create a portion that is larger than the openings in the hub to lock the hook and hub in place. Further still, a suture or cable may be secured to each hook, tensioned, and then tied off on the hub to lock the relative position of the hub and hooks.

As a further alternative embodiment, the hooks may be comprises of a malleable material, such as stainless steel or other implantable materials, which is formed in a first configuration and passed through the hub and the everted end of the first tissue structure, inserted into the opening in the second tissue structure, and then mechanically deformed to a desired anchoring configuration which exerts compressive force on the respective tissue structures. A secondary mechanism for applying and maintaining tension on the hooks, as discussed above, may be used with this embodiment as well.

As yet another alternative embodiment, the hooks may be comprised of a fairly rigid material formed in a first configuration, temporarily deformed into a second configuration in order to pass part of each hook through the opening in the second tissue structure, and then released to assume the first configuration to clamp the respective tissue structures. For example, the hooks could be L-shaped as shown in FIGS. 29A–30B, and forced into a sheath having a diameter that permits it to be passed through the opening O in the second tissue structure. After the leg of each hook has been sufficiently passed into the opening, the sheath could be removed to allow the hooks to assume the L-shape and clamp the tissue structures.

The anastomosis systems disclosed above are preferably used while the patient is on cardiopulmonary bypass, which may be established as disclosed in U.S. Pat. No. 5,584,803, the subject matter of which is incorporated by reference. It will be appreciated, however, that the systems may be used while the patient's heart is beating by utilizing instruments which serve to isolate at least a portion of the vascular conduits being anastomosed from blood flowing therethrough.

Many variations and modifications of the devices and methods disclosed herein will be readily apparent to persons skilled in the art. As such, it should be understood that the foregoing detailed description of preferred embodiments is made for purposes of setting forth a clear and complete disclosure, and is not intended to limit the scope of the invention which is defined by the claims which follow.

What is claimed is:

1. A method for anastomosing one hollow tissue structure to another hollow tissue structure, the method comprising steps of:

passing a first portion of at least one anastomosis device through an end of a first hollow tissue structure, the anastomosis device being in a first configuration;

positioning the end of the first hollow tissue structure and the first portion of the anastomosis device through an opening formed in a wall of a second hollow tissue structure;

securing the first and second hollow tissue structures together by changing the configuration of the anastomosis device to compress the end of the first hollow tissue structure against the wall of the second hollow tissue structure without penetrating the anastomosis device into an inner wall of the second hollow tissue structure, wherein the first hollow tissue structure is secured in communication with the opening in the second hollow tissue.

2. The method of claim 1, wherein the securing step is carried out by deforming the first portion of the anastomosis device against an inner surface of the wall of the second hollow tissue structure so that the end of the first hollow tissue structure and the wall of the second hollow tissue structure are compressed between the first portion and a second portion of the anastomosis device.

3. A method for anastomosing one hollow tissue structure to another hollow tissue structure, the method comprising steps of:

passing a first portion of at least one anastomosis device through an end of a first hollow tissue structure, the anastomosis device being in a first configuration;

positioning the end of the first hollow tissue structure and the first portion of the anastomosis device through an opening formed in a wall of a second hollow tissue structure; and securing the first and second hollow tissue structures together by changing the configuration of the anastomosis device to compress the end of the first hollow tissue structure against the wall of the second hollow tissue structure without passing the anastomosis device through the second hollow tissue structure, wherein the first hollow tissue structure is secured in communication with the opening in the second hollow tissue;

wherein a plurality of separate, unconnected anastomosis devices are used to secure the end of the first hollow tissue structure to the second hollow tissue structure.

4. A method for anastomosing one hollow tissue structure to another hollow tissue structure, the method comprising steps of:

passing a first portion of at least one anastomosis device through an end of a first hollow tissue structure, the anastomosis device being in a first configuration;

positioning the end of the first hollow tissue structure and the first portion of the anastomosis device through an opening formed in a wall of a second hollow tissue structure;

securing the first and second hollow tissue structures together by changing the configuration of the anastomosis device to compress the end of the first hollow tissue structure against the wall of the second hollow tissue structure without passing the anastomosis device through the second hollow tissue structure, wherein the first hollow tissue structure is secured in communication with the opening in the second hollow tissue;

wherein each anastomosis device is generally L-shaped when in the first configuration and is generally C-shaped after said securing step.

5. A method for anastomosing one hollow tissue structure to another hollow tissue structure, the method comprising steps of:

providing a first hollow tissue structure having a lumen and an end adapted to be anastomosed to a second hollow tissue structure;

forming an opening in the second hollow tissue structure;

providing a tissue securing element having first and second ends, at least the first end being configured to be passed through tissue, wherein the tissue securing element is configured in a first orientation and is comprised of a material capable of being deformed to a second orientation which is different from the first orientation;

passing the first end of the tissue securing element through the end of the first hollow tissue structure;

positioning the first end of the tissue securing element and the end of the first hollow tissue structure within the opening in the second hollow tissue structure; and deforming the tissue securing element to the second orientation to compress the end of the first hollow tissue structure against the second hollow tissue structure without penetrating an external wall of the second hollow tissue structure.

6. The method of claim 5, wherein the first hollow tissue structure is a vascular conduit and the second hollow body structure is a patient's aorta.

7. The method of claim 5, wherein said passing step is carried out by everting the end of the first hollow tissue structure and passing the first end of the tissue securing element through the everted end from an exterior surface of the first hollow tissue structure toward an interior surface of the first hollow tissue structure.

8. The method of claim 5, wherein said deforming step is carried out so that the first end of the tissue securing element partially penetrates the second hollow tissue structure.

9. An anastomosis system comprising:

an applier comprising first and second relatively movable members;

a plurality of separate, unconnected tissue securing members removably supported by at least one of first and second members, each tissue securing member having opposite ends one of which is configured to passed through a first hollow tissue structure, wherein each tissue securing member is in a first configuration;

wherein the first and second members of the applier are moved relative to each other to form each tissue securing member into a second configuration which is different from the first configuration and compresses the first and second hollow tissue structures.

10. The anastomosis system of claim 9, wherein the tissue securing members are comprised of a rigid material formed in said first configuration and are permanently deformed into said second configuration by moving the first and second members of the applier relative to each other.

11. The anastomosis system of claim 9, wherein the tissue securing members are comprised of superelastic material formed in said second configuration and are resiliently biased from said second configuration into said first configuration by moving the first and second members of the applier relative to each other.

12. The anastomosis system of claim 9, wherein the tissue securing members are comprised of a rigid material oriented in said second configuration and are repositioned so as to be oriented in said second configuration by moving the first and second members of the applier relative to each other.

13. The anastomosis system of claim 9, further comprising a hub through which the tissue securing members are positioned.

* * * * *